(12) United States Patent
Oraevsky et al.

(10) Patent No.: US 10,709,419 B2
(45) Date of Patent: Jul. 14, 2020

(54) DUAL MODALITY IMAGING SYSTEM FOR COREGISTERED FUNCTIONAL AND ANATOMICAL MAPPING

(71) Applicant: Seno Medical Instruments, Inc., San Antonio, TX (US)

(72) Inventors: Alexander A. Oraevsky, Houston, TX (US); Sergey A. Ermilov, Houston, TX (US); Andre Conjusteau, Houston, TX (US); Peter Brecht, Santa Monica, CA (US); Vyacheslav Nadvoretskiy, Houston, TX (US); Richard Su, Sugar Land, TX (US); Donald G. Herzog, Collingswood, NJ (US); Bryan Clingman, Chandler, AZ (US); Jason Zalev, Thornhill (CA)

(73) Assignee: SENO MEDICAL INSTRUMENTS, INC., San Antonio, TX (US)

( * ) Notice: Subject to any disclaimer, the term of this patent is extended or adjusted under 35 U.S.C. 154(b) by 0 days.

(21) Appl. No.: 15/277,835

(22) Filed: Sep. 27, 2016

(65) Prior Publication Data

US 2017/0014101 A1   Jan. 19, 2017

Related U.S. Application Data

(63) Continuation of application No. 13/667,808, filed on Nov. 2, 2012, now abandoned, which is a
(Continued)

(51) Int. Cl.
*A61B 8/00* (2006.01)
*A61B 5/00* (2006.01)
(Continued)

(52) U.S. Cl.
CPC .......... *A61B 8/4416* (2013.01); *A61B 5/0035* (2013.01); *A61B 5/0095* (2013.01);
(Continued)

(58) Field of Classification Search
CPC ...... A61B 2090/306; A61B 2562/0238; A61B 5/0035; A61B 5/0095; A61B 5/14542;
(Continued)

(56) References Cited

U.S. PATENT DOCUMENTS 4,116,797 A   9/1978   Akatsuka
4,267,732 A   5/1981   Quate
(Continued)

FOREIGN PATENT DOCUMENTS

EP   0282234 A1   9/1988
EP   1493380 A1   1/2005
(Continued)

OTHER PUBLICATIONS

Su et al. "Boundary Effects Reduction in Wavelet Transform for Time-frequency analysis." WSEAS Transactions on Signal Processing: 4(8), pp. 169-179. Oct. 2012. (Year: 2012).*
(Continued)

*Primary Examiner* — Amelie R Davis
(74) *Attorney, Agent, or Firm* — The Small Patent Law Group LLP; Josef L. Hoffmann

(57) ABSTRACT

A real-time imaging system that provides ultrasonic imaging and optoacoustic imaging coregistered through application of the same hand-held probe to generate and detect ultrasonic and optoacoustic signals. These signals are digitized, processed and used to reconstruct anatomical maps superimposed with maps of two functional parameters of blood hemoglobin index and blood oxygenation index. The blood hemoglobin index represents blood hemoglobin concentration changes in the areas of diagnostic interest relative to the
(Continued)

background blood concentration. The blood oxygenation index represents blood oxygenation changes in the areas of diagnostic interest relative to the background level of blood oxygenation. These coregistered maps can be used to non-invasively differentiate malignant tumors from benign lumps and cysts.

9 Claims, 28 Drawing Sheets

Related U.S. Application Data continuation-in-part of application No. 13/507,217, filed on Jun. 13, 2012, now Pat. No. 9,289,191, which is a continuation-in-part of application No. 13/341,950, filed on Dec. 31, 2011, now Pat. No. 8,686,335, which is a continuation-in-part of application No. 13/287,759, filed on Nov. 2, 2011, now abandoned.

(51) Int. Cl.
A61B 8/08 (2006.01)
A61B 5/145 (2006.01)
A61B 5/1455 (2006.01)
A61B 8/14 (2006.01)
A61B 90/30 (2016.01)

(52) U.S. Cl.
CPC ...... A61B 5/14542 (2013.01); A61B 5/14546 (2013.01); A61B 5/14552 (2013.01); A61B 5/7425 (2013.01); A61B 8/085 (2013.01); A61B 8/0825 (2013.01); A61B 8/0891 (2013.01); A61B 8/14 (2013.01); A61B 8/4444 (2013.01); A61B 8/463 (2013.01); A61B 8/5261 (2013.01); A61B 5/726 (2013.01); A61B 2090/306 (2016.02); A61B 2562/0238 (2013.01)

(58) Field of Classification Search
CPC ............ A61B 5/14546; A61B 5/14552; A61B 5/7425; A61B 8/0825; A61B 8/085; A61B 8/0891; A61B 8/14; A61B 8/4416; A61B 8/4444; A61B 8/463; A61B 8/5261
See application file for complete search history.

(56) References Cited

U.S. PATENT DOCUMENTS

| | | | |
|---|---|---|---|
| 4,651,850 A | 3/1987 | Matsuo | |
| 5,293,873 A | 3/1994 | Fang | |
| 5,341,204 A | 8/1994 | Grant et al. | |
| 5,348,002 A | 9/1994 | Caro | |
| 5,427,105 A | 6/1995 | Knapp et al. | |
| 5,460,182 A | 10/1995 | Goodman et al. | |
| 5,504,281 A | 4/1996 | Whitney et al. | |
| 5,674,218 A | 10/1997 | Rubinsky et al. | |
| 5,713,356 A | 2/1998 | Kruger | |
| 5,754,676 A | 5/1998 | Komiya et al. | |
| 5,830,146 A | 11/1998 | Skladnev et al. | |
| 5,840,023 A | 11/1998 | Oraevsky et al. | |
| 5,935,288 A | 8/1999 | DiGiovanni et al. | |
| 5,977,538 A | 11/1999 | Unger et al. | |
| 6,094,050 A * | 7/2000 | Zaroubi | G01R 33/56 324/307 |
| 6,216,025 B1 | 4/2001 | Kruger | |
| 6,263,094 B1 | 7/2001 | Rosich et al. | |
| 6,617,559 B1 | 9/2003 | Emery et al. | |
| 6,694,157 B1 | 2/2004 | Stone et al. | |
| 6,751,490 B2 | 6/2004 | Esenaliev et al. | |
| 6,827,686 B2 | 12/2004 | Szabo et al. | |
| 6,979,292 B2 | 12/2005 | Kanayama et al. | |
| 7,675,013 B2 | 3/2010 | Kobayashi et al. | |
| 7,741,900 B1 | 6/2010 | Li | |
| 7,972,272 B2 | 7/2011 | Munce et al. | |
| 8,016,419 B2 | 9/2011 | Zhang et al. | |
| 8,025,406 B2 | 9/2011 | Zhang et al. | |
| 8,109,981 B2 | 2/2012 | Gertner et al. | |
| 8,144,327 B2 | 3/2012 | Nakajima et al. | |
| 8,214,010 B2 | 7/2012 | Courtney et al. | |
| 8,298,144 B2 | 10/2012 | Burcher | |
| 8,300,224 B2 | 10/2012 | Nakajima et al. | |
| 8,327,973 B2 | 12/2012 | Parish et al. | |
| 8,353,830 B2 | 1/2013 | Kanayama et al. | |
| 8,353,833 B2 | 1/2013 | Dogra et al. | |
| 8,460,195 B2 | 6/2013 | Courtney et al. | |
| 8,480,584 B2 | 7/2013 | Kanayama et al. | |
| 8,519,998 B2 | 8/2013 | Hashimoto et al. | |
| 8,686,335 B2 | 4/2014 | Schmid et al. | |
| 8,712,506 B2 | 4/2014 | Courtney et al. | |
| 8,823,928 B2 | 9/2014 | Herzog et al. | |
| 8,870,770 B2 | 10/2014 | Dogra et al. | |
| 8,876,717 B2 | 11/2014 | Tokita et al. | |
| 9,128,032 B2 | 9/2015 | Carson et al. | |
| 9,163,980 B2 | 10/2015 | Herzog et al. | |
| 9,226,666 B2 | 1/2016 | Wang et al. | |
| 9,282,899 B2 | 3/2016 | Zalev | |
| 9,289,191 B2 | 3/2016 | Clingman et al. | |
| 9,330,452 B2 | 5/2016 | Zalev et al. | |
| 9,357,923 B2 | 6/2016 | Courtney et al. | |
| 9,375,147 B2 | 6/2016 | Courtney et al. | |
| 9,445,785 B2 | 9/2016 | Clingman et al. | |
| 9,445,786 B2 | 9/2016 | Zalev et al. | |
| 9,456,805 B2 | 10/2016 | Zalev et al. | |
| 9,517,055 B2 | 12/2016 | Zalev | |
| 9,528,936 B2 | 12/2016 | Schmid | |
| 9,700,214 B2 | 7/2017 | Ichihara et al. | |
| 2001/0012429 A1* | 8/2001 | Wach | A61B 5/14546 385/115 |
| 2001/0022657 A1 | 9/2001 | Autrey et al. | |
| 2003/0139672 A1 | 7/2003 | Cane et al. | |
| 2004/0039379 A1* | 2/2004 | Viator | A61B 18/203 606/9 |
| 2004/0167619 A1 | 8/2004 | Case et al. | |
| 2005/0004458 A1 | 1/2005 | Kanayama et al. | |
| 2005/0070801 A1 | 3/2005 | Yamashita et al. | |
| 2005/0105877 A1 | 5/2005 | Nappi et al. | |
| 2005/0187471 A1 | 8/2005 | Kanayama et al. | |
| 2005/0261568 A1 | 11/2005 | Hular et al. | |
| 2006/0167531 A1 | 7/2006 | Gertner et al. | |
| 2007/0081711 A1 | 4/2007 | Kim et al. | |
| 2007/0093702 A1 | 4/2007 | Yu et al. | |
| 2007/0093708 A1 | 4/2007 | Benaron et al. | |
| 2007/0238958 A1 | 10/2007 | Oraevsky et al. | |
| 2008/0051655 A1 | 2/2008 | Sato et al. | |
| 2008/0071172 A1 | 3/2008 | Bruck et al. | |
| 2008/0154130 A1 | 6/2008 | Weiss et al. | |
| 2008/0172111 A1 | 7/2008 | Anderson et al. | |
| 2008/0177183 A1 | 7/2008 | Courtney et al. | |
| 2008/0243001 A1 | 10/2008 | Oakley et al. | |
| 2008/0255433 A1 | 10/2008 | Prough et al. | |
| 2009/0000383 A1 | 1/2009 | Knowles et al. | |
| 2009/0024038 A1 | 1/2009 | Arnold | |
| 2009/0124902 A1 | 5/2009 | Herrmann | |
| 2009/0149761 A1 | 6/2009 | Zou et al. | |
| 2009/0156932 A1 | 6/2009 | Zharov | |
| 2009/0157002 A1 | 6/2009 | Dumot et al. | |
| 2009/0187099 A1 | 7/2009 | Burcher | |
| 2009/0263001 A1 | 10/2009 | Ding et al. | |
| 2010/0016717 A1 | 1/2010 | Dogra et al. | |
| 2010/0049044 A1 | 2/2010 | Burcher | |
| 2010/0053618 A1 | 3/2010 | Nakajima et al. | |
| 2010/0056916 A1 | 3/2010 | Bakker et al. | |
| 2010/0094134 A1 | 4/2010 | Zhu et al. | |
| 2010/0154547 A1 | 6/2010 | Fukada et al. | |
| 2010/0174190 A1 | 7/2010 | Hancock et al. | |
| 2010/0249570 A1 | 9/2010 | Carson et al. | |
| 2010/0256496 A1 | 10/2010 | Zhu | |
| 2010/0268042 A1 | 10/2010 | Wang et al. | |
| 2010/0285518 A1 | 11/2010 | Viator et al. | |
| 2010/0298688 A1 | 11/2010 | Dogra et al. | |

(56) References Cited

U.S. PATENT DOCUMENTS

| | | |
|---|---|---|
| 2011/0054292 A1 | 3/2011 | Hirson et al. |
| 2011/0088477 A1 | 4/2011 | Someda et al. |
| 2011/0091423 A1 | 4/2011 | Kempf et al. |
| 2011/0098572 A1 | 4/2011 | Chen et al. |
| 2011/0106478 A1 | 5/2011 | Someda |
| 2011/0118606 A1 | 5/2011 | Kim |
| 2011/0125024 A1 | 5/2011 | Mueller et al. |
| 2011/0178401 A1 | 7/2011 | Ichihara et al. |
| 2011/0201914 A1 | 8/2011 | Wang et al. |
| 2011/0231160 A1 | 9/2011 | Suzuki |
| 2011/0239766 A1 | 10/2011 | Nakajima et al. |
| 2011/0303015 A1 | 12/2011 | Ichihara et al. |
| 2011/0306857 A1 | 12/2011 | Razansky et al. |
| 2011/0307181 A1 | 12/2011 | Nagae |
| 2011/0319743 A1 | 12/2011 | Satoh |
| 2012/0065516 A1 | 3/2012 | Nishikubo et al. |
| 2012/0095343 A1* | 4/2012 | Smith ............... A61B 8/58 600/447 |
| 2012/0165677 A1 | 6/2012 | Li et al. |
| 2012/0167693 A1 | 7/2012 | Asao |
| 2012/0289812 A1 | 11/2012 | Oishi |
| 2012/0300961 A1* | 11/2012 | Moeller ............. H04R 3/00 381/122 |
| 2013/0039147 A1 | 2/2013 | Witte et al. |
| 2013/0041267 A1 | 2/2013 | Ntziachristos et al. |
| 2013/0060140 A1 | 3/2013 | Sinelnikov |
| 2013/0064771 A1 | 3/2013 | Wada |
| 2013/0109950 A1 | 5/2013 | Herzog et al. |
| 2013/0112001 A1 | 5/2013 | Furukawa |
| 2013/0116538 A1 | 5/2013 | Herzog et al. |
| 2013/0190591 A1 | 7/2013 | Hirson et al. |
| 2013/0190595 A1 | 7/2013 | Oraevsky et al. |
| 2013/0245420 A1* | 9/2013 | Fukutani ............ A61B 5/0095 600/407 |
| 2013/0279920 A1 | 10/2013 | Herzog |
| 2013/0281819 A1 | 10/2013 | Schmid |
| 2013/0289381 A1 | 10/2013 | Oraevsky et al. |
| 2013/0296683 A1 | 11/2013 | Herzog et al. |
| 2013/0296684 A1 | 11/2013 | Miller et al. |
| 2013/0296701 A1 | 11/2013 | Zalev et al. |
| 2013/0301380 A1 | 11/2013 | Oraevsky et al. |
| 2013/0303875 A1 | 11/2013 | Joy et al. |
| 2013/0304405 A1 | 11/2013 | Schmid et al. |
| 2013/0310688 A1 | 11/2013 | Rosen et al. |
| 2013/0335441 A1 | 12/2013 | Zalev et al. |
| 2014/0005544 A1 | 1/2014 | Zalev et al. |
| 2014/0007690 A1 | 1/2014 | Hirota |
| 2014/0051969 A1 | 2/2014 | Suzuki |
| 2014/0145648 A1* | 5/2014 | Tokita ............... A61B 5/0073 315/362 |
| 2014/0187902 A1 | 7/2014 | Sato et al. |
| 2014/0194723 A1 | 7/2014 | Herzog et al. |
| 2014/0198606 A1 | 7/2014 | Morscher et al. |
| 2014/0206978 A1 | 7/2014 | Ackerman et al. |
| 2014/0219530 A1 | 8/2014 | Zalev |
| 2014/0221810 A1 | 8/2014 | Kacprowicz |
| 2014/0249414 A1 | 9/2014 | Herzog et al. |
| 2014/0303476 A1 | 10/2014 | Dogra et al. |
| 2014/0323860 A1 | 10/2014 | Courtney et al. |
| 2015/0297090 A1 | 10/2015 | Herzog et al. |
| 2016/0199037 A1 | 7/2016 | Clingman et al. |
| 2016/0249812 A1 | 9/2016 | Wang et al. |
| 2016/0296121 A1 | 10/2016 | Herzog et al. |
| 2016/0302763 A1 | 10/2016 | Courtney et al. |
| 2016/0317034 A1 | 11/2016 | Zalev et al. |
| 2016/0317038 A1 | 11/2016 | Zalev et al. |
| 2017/0000354 A1 | 1/2017 | Zalev et al. |
| 2017/0014101 A1 | 1/2017 | Oraevsky et al. |
| 2017/0035388 A1 | 2/2017 | Herzog et al. |
| 2017/0112474 A1 | 4/2017 | Burcher |

FOREIGN PATENT DOCUMENTS

| | | |
|---|---|---|
| JP | H07284090 A | 10/1995 |
| JP | H11-076232 A | 3/1999 |
| JP | 2005218684 A | 8/2005 |
| JP | 2005536309 A | 12/2005 |
| JP | 2007267837 A | 10/2007 |
| JP | 2008049063 A | 3/2008 |
| JP | 2009512500 A | 3/2009 |
| JP | 2009082469 A | 4/2009 |
| JP | 2010509977 A | 4/2010 |
| JP | 2010125260 A | 6/2010 |
| JP | 2010136887 A | 6/2010 |
| JP | 2010167167 A | 8/2010 |
| JP | 2010200926 A | 9/2010 |
| JP | 2011072702 A | 4/2011 |
| JP | 2011083531 A | 4/2011 |
| JP | 2011097991 A | 5/2011 |
| JP | 2011519281 A | 7/2011 |
| JP | 2011177496 A | 9/2011 |
| JP | 2011193914 A | 10/2011 |
| JP | 2013-202050 A | 10/2013 |
| JP | 2013-255707 A | 12/2013 |
| WO | 0110295 A1 | 2/2001 |
| WO | 2004010866 A1 | 2/2004 |
| WO | 2006061829 A1 | 6/2006 |
| WO | 2010009747 A1 | 1/2010 |
| WO | 2010045421 A2 | 4/2010 |
| WO | 2010127199 A1 | 11/2010 |
| WO | 2011027548 A1 | 3/2011 |
| WO | 2011091423 A2 | 7/2011 |
| WO | 2011098101 A1 | 8/2011 |
| WO | 2011137385 A1 | 11/2011 |
| WO | 2013067383 A1 | 5/2013 |
| WO | 2013067419 A1 | 5/2013 |
| WO | 2013112626 A1 | 8/2013 |
| WO | 2013158154 A1 | 10/2013 |
| WO | 2013/188711 A1 | 12/2013 |
| WO | 2013/188714 A1 | 12/2013 |
| WO | 2013188707 A1 | 12/2013 |
| WO | 2013188708 A1 | 12/2013 |
| WO | 2013188709 A1 | 12/2013 |
| WO | 2013188710 A1 | 12/2013 |
| WO | 2013188713 A1 | 12/2013 |
| WO | 2014116705 A1 | 7/2014 |

OTHER PUBLICATIONS

Delta Function explanation. http://mathworld.wolfram.com/DeltaFunction.html (Year: 2019).*
"MATLAB: Programming Fundamentals", The Math Works, Inc., R2011 b, 2011.
Aziz et al. 2011 Optik 122:1462-1465.
Castelino, Robin; "Biomedical Applications of Photoacoustics for Thermal Therapy", 2008.
Dahl, Jeremy J. and Trahey, Gregg E., "Off-Axis Scatterer Filters for Improved Aberration Measurements", 2003 IEEE Ultrasonics Symposium—344, 2003.
Emelianov, Stanislav Y., et al. "Combined ultrasound, optoacoustic, and elasticity imaging." Biomedical Optics 2004. International Society for Optics and Photonics, 2004.
Ermilov, Sergey A., et al. "Development of laser optoacoustic and ultrasonic imaging system for breast cancer utilizing handheld array probes." SPIE BiOS: Biomedical Optics. International Society for Optics and Photonics, 2009.
Esenaliev, Rinat O., et al. "Laser optoacoustic tomography for medical diagnostics: experiments with biological tissues." Photonics West'96. International Society for Optics and Photonics, 1996.
Fronheiser et al. 2010 J. Biomed. Optics 15:021305-1-021305-7.
Holan, Scott H., and John A. Viator. "Automated wavelet denoising of photoacoustic signals for circulating melanoma cell detection and burn image reconstruction." Physics in medicine and biology 53.12 (2008): N227.
Inada K: "Basic Componenets and Fiber Optic Passive Components: Status and Trends in Japan", IEEE Journal on Selected Areas

(56) References Cited

OTHER PUBLICATIONS in Communications, IEEE Service Center, Piscataway, US, vol. SAC-04, No. 4, Jul. 1, 1986 (Jul. 1, 1986), pp. 472-479.
Intel, Intel Integrated Performance Primitives for Intel Architecture, Reference Manual, vol. 2: Image and Video Processing, Sep. 2007.
Jiang Zhen et al: "Different optical spectral characteristics in a necrotic transmissible venereal tumor and a cystic lesion in the same canine prostate observed by triple-band trans-rectal optical tomography under trans-rectal ultrasound guidance", Multimodal Biomedical Imaging VI, SPIE, 1000 20th St. Bellingham Wa 98225-6705 USA, vol. 7892, No. 1, Feb. 10, 2011 (Feb. 10, 2011), pp. 1-10.
Karabutov, A.; Letokhov, V.; and Podymova, N.: Time-resolved opto-acoustic tomography of inhomogeneous media; SPIE vol. 2389, pp. 209-217 (1995).
Kingsbury, "Complex Wavelets for Shift Invariant Analysis and Filtering of Signals", Journal of Applied and Computational Harmonic Analysis, vol. 10, No. 3, May 2001, pp. 234-253.
Kuchment, P. et al., "Mathematics of Photoacoustic and Thermoacoustic Tomography", Mathematics Dept., Texas A&M University, Dec. 10, 2009.
Ma, Rui, et al. "Multispectral optoacoustic tomography (MSOT) scanner for whole-body small animal imaging." Optics express 17.24 (2009): 21414-21426.
Misiti, Michel et al., "Wavelet Toolbox", The MathWorks, Inc., User's Guide, Version 1, 1996.
Munch, Beat et al., "Stripe and ring artifact removal with combined wavelet—Fourier filtering", Optics Express 8567, vol. 17, No. 10, May 11, 2009.
Needles A et al: "Development and validation of a combined photoacoustic micro-ultrasound system foroxygen saturation estimation", Photons Plus Ultrasound: Imaging and Sensing 2011, SPIE, 1000 20th St. Bellingham WA 98225-6705 USA, vol. 7899, No. 1, Feb. 10, 2011 (Feb. 10, 2011), pp. 1-8.
Nguyen, "A Family of Inversion Formulas in Thermoacoustic Tomography", Department of Mathematics, Texas A&M University, Mar. 5, 2009.
Niederhauser et al. "Combined Ultrasound and Optoacoustic System for Real-Time High-Contrast Vascular Imaging in Vivo," IEEE Trans. Med. Imaging, vol. 24, No. 4, pp. 436-440, 2005.
Niederhauser, Joel J., Michael Jaeger, and Martin Frenz. "Comparision of laser-induced and classical ultasound." Biomedical Optics 2003. International Society for Optics and Photonics, 2003.
O'Donnell, Matthew et al., "Correlation-Based Aberration Correction in the Presence of Inoperable Elements", IEEE Transactions of Ultrasonics, Ferroelectrics, and Frequency Control, vol. 39, No. 6, Nov. 1992.
Oraevsky, A. A., et al. "Time-resolved optoacoustic imaging in layered biological tissues." Advances in optical imaging and photon migration 21 (1994): 161-165.
Oraevsky, Alexander A., et al. "Direct measurement of laser fluence distribution and optoacoustic imaging in heterogeneous tissues." International Symposium on Biomedical Optics Europe'94. International Society for Optics and Photonics, 1995.
Oraevsky, Alexander A., et al. "Laser optoacoustic tomography for medical diagnostics: Principles." Photonics West'96. International Society for Optics and Photonics, 1996.
Oraevsky, Alexander A., et al. "Lateral and z-axial resolution in laser optoacoustic imaging with ultrasonic transducers." Photonics West'95. International Society for Optics and Photonics, 1995.
Oraevsky, Alexander A., Steven L. Jacques, and Frank K. Tittel. "Determination of tissue optical properties by piezoelectric detection of laser-induced stress waves." OE/LASE'93: Optics, Electro-Optics, & Laser Applications in Science& Engineering. International Society for Optics and Photonics, 1993.
Otto et al., "Coregistration of Angiogenesis Related Hemoglobin and Tissue Density in breast tumors using opto-acoustic imaging combined with ultrasound", 2009.
Quing Zhu et al: "Optical Tomography with Ultrasound imaging probe comprising a light emitting portion and an array of Localization for Breast Cancer Diagnosis and Treatment Monitoring", NIH Public Access Author Manuscript PMC2133371, Apr. 1, 2008 (Apr. 1, 2008), pp. 1-18.
Sendur et al., "Bivariate Shrinkage Functions for Wavelet-Based Denoising Exploiting Interscale Dependency", IEEE Transactions on Signal Processing, vol. 50, No. 11, Nov. 2002.
Tao Lu et al: "Deconvolution Algorithm with LTI Wiener Filter in Photoacousic Tomography", Photonics and Optoelectronics, 2009. SOPO 2009. Symposium on, IEEE Express Conference Publishing, Piscataway, NJ, USA, Aug. 14, 2009 (Aug. 14, 2009), pp. 1-4.
Xueding Wang et al: "Noninvasive imaging of hemoglobin concentration and oxygenation in the rat brain using high-resolution photoacoustic tomography", Journal of Biomedical Optics, vol. 11, No. 2, May 3, 2006 (May 3, 2006), p. 024015, XP055202984, ISSN: 1083-3668, DOI : 10.1117/1.2192804.
Yamashita Y et al: "Low Sound Velocity and Acoustic Attenuation Silicone Rubber Lens Based on Nano-Powder-Composite for Medical Echo Ultrasound Array Probes", Applications of Ferroelectrics, 2007. ISAF 2007. Sixteenth IEEE International Symposium on, IEEE, PI,May 31, 2007 (May 31, 2007), pp. 752-753.
Yi Wang et al: "Photoacoustic imaging with deconvolution algorithm; Photoacoustic imaging with deconvolution algorithm", Physics in Medicine and Biology, Institute of Physics Publishing, Bristol GB, vol. 49, No. 14, Jul. 21, 2004 (Jul. 21, 2004), pp. 3117-3124.
Yu Wang et al: "Integrated Photoacoustic and Fluorescence Confocal Microscopy", IEEE Transactions on Biomedical Engineering, IEEE Service Center, Piscataway, NJ, USA, vol. 57, No. 10, Sep. 15, 2010 (Sep. 15, 2010), pp. 2576-2578.
Ermilov, Sergey A., et al. "Laser optoacoustic imaging system for detection of breast cancer." Journal of biomedical optics 14.2 (2009): 024007-024007.
Hamilton, James D., et al. "High frequency optoacoustic arrays using etalon detection." IEEE transactions on ultrasonics, ferroelectrics, and frequency control 47.1 (2000): 160-169.
Kossoff et al. "Average velocity of ultrasound in the human female breast." The Journal of Acoustical Society of America 53.6 (1973): 1730-1736.
Japanese Office Action for corresponding JP Application No. 2018074832, dated Mar. 5, 2019 (8 pages).

* cited by examiner

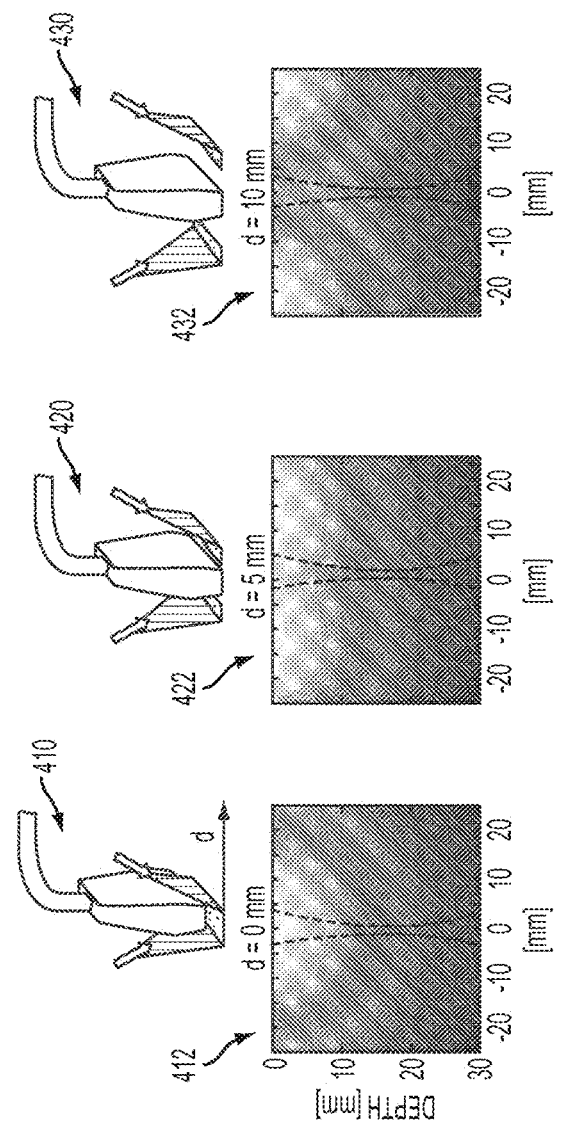

DUAL MODALITY IMAGING SYSTEM FOR COREGISTERED FUNCTIONAL AND ANATOMICAL MAPPING

This application is a continuation of U.S. patent application Ser. No. 13/667,808, filed Nov. 2, 2012, entitled "Dual Modality Imaging System For Coregistered Functional And Anatomical Mapping," which is a continuation-in-part of U.S. patent application Ser. No. 13/507,217, filed Jun. 13, 2012, entitled "System and Method for Acquiring Optoacoustic Data and Producing Parametric Maps Thereof" and is a continuation-in-part of U.S. patent application Ser. No. 13/341,950, filed Dec. 31, 2011, entitled "System and Method for Adjusting the Light Output of an Optoacoustic Imaging System" and is a continuation-in-part of U.S. patent application Ser. No. 13/287,759, filed Nov. 2, 2011, entitled "Handheld Optoacoustic Probe." The entire disclosures of those applications, including the appendices thereof, are incorporated herein by reference.

FIELD OF THE TECHNOLOGY

At least some embodiments disclosed herein relate, in general, to systems for biomedical imaging, and more particularly, to real-time imaging systems that visualize thin tissue slices noninvasively through skin.

BACKGROUND

Medical ultrasound imaging is a well-established imaging technology for visualization of tissue morphology in various organs that provides diagnostic information based on analysis of anatomy. Optoacoustic imaging is used in medical applications for in vivo and in vitro mapping of animal and human tissues and organs based on variation in tissue optical properties. Optoacoustic tomography can provide anatomical, functional and molecular imaging, but the most significant value of optoacoustic imaging is in its capability to provide quantitative functional information based on endogenous contrast of molecular constituents of red blood cells. The essence of functional imaging is to provide the physician with a map of blood distribution and its level of oxygenation, so that the physician can determine whether particular tissue functions normally or not. For example, a map of total hemoglobin distribution simultaneously showing an area with increased concentration and decreased oxygen saturation indicates potential malignancy. The essence of molecular imaging is to provide maps of distributions and concentrations of various molecules of interest for a specific health condition. For example, distribution of specific protein receptors in cell membranes gives insight into molecular biology or cells that aids in designing drugs and therapeutic methods to treating human diseases.

SUMMARY

In an embodiment, the invention provides a real-time imaging system that visualizes thin tissue slices noninvasively through skin and provides three independent and co-registered images with biomedically significant information. Specifically, images of deep biological tissue structures are precisely superimposed with images of tissue functional state, such as the total hemoglobin concentration and blood level of oxygen saturation. The invention in this embodiment thus combines ultrasonic imaging and optoacoustic imaging technologies in a novel manner. These technologies can advantageously be combined given the complementary nature of information provided by them, and the fact that the same set of ultrasonic/pressure detectors and the same set of analog and digital electronics can be used to acquire both types of signals from tissues. In order to achieve a high level of accuracy of quantitative information and present it substantially in real time (i.e. substantially as it occurs), a design is disclosed that utilizes one or more dual-wavelength short-pulse lasers or a plurality of single-wavelength short pulse lasers, a fiberoptic light delivery system, a hand-held imaging probe, other electronic hardware and processing software.

In an embodiment, an imaging system is disclosed for visualization of slices into the depth of tissue of at least a portion of a body. The system includes a processing subsystem that produces three independent images, including two functional images showing distribution of the total hemoglobin concentration and distribution of the blood oxygen saturation and one morphological image of tissue structures, the images being co-registered in time and space by utilizing one and the same hand-held imaging probe. The system may include a three-dimensional positioning system which provides the capability of assembling three dimensional volumetric images of said body from two-dimensional slices made though the depth of tissue obtained by scanning a hand-held probe along the surface of at least portion of the body.

In an embodiment, an imaging method provides coregistered functional and anatomical mapping of tissue of at least a portion of a body. Ultrasonic pulses are delivered into the tissue and backscattered ultrasonic signals reflected from various structural tissue boundaries associated with body morphology are detected. Two optical pulses having different spectral bands of electromagnetic energy are delivered, and transient ultrasonic signals resulting from selective absorption of different energy fractions from each of the two optical pulses by hemoglobin and oxyhemoglobin of blood containing tissues are detected. Detected ultrasonic signals are processed to remove noise, to revert signal alterations in the course of signal propagation through tissue and through the detection system components, and to restore the temporal shape and ultrasonic spectrum of the original signals. Image reconstruction and processing is performed to generate morphological images of tissue structures coregistered and superimposed with partially transparent functional images of the total hemoglobin concentration and blood oxygen saturation. The above steps of the process are repeated with a video frame rate so that real-time images can display tissue functional and morphological changes substantially as they occur.

BRIEF DESCRIPTION OF THE DRAWINGS

The disclosed embodiments are illustrated by way of example and not limitation in the figures of the accompanying drawings in which like references indicate similar elements.

FIGS. 4A-4C illustrate embodiments wherein optical illumination of tissue is accomplished using a hand-held optoacoustic probe that delivers optical energy from either under the optoacoustic probe or on the side of the probe at different distances.

DETAILED DESCRIPTION

Figure 1A:
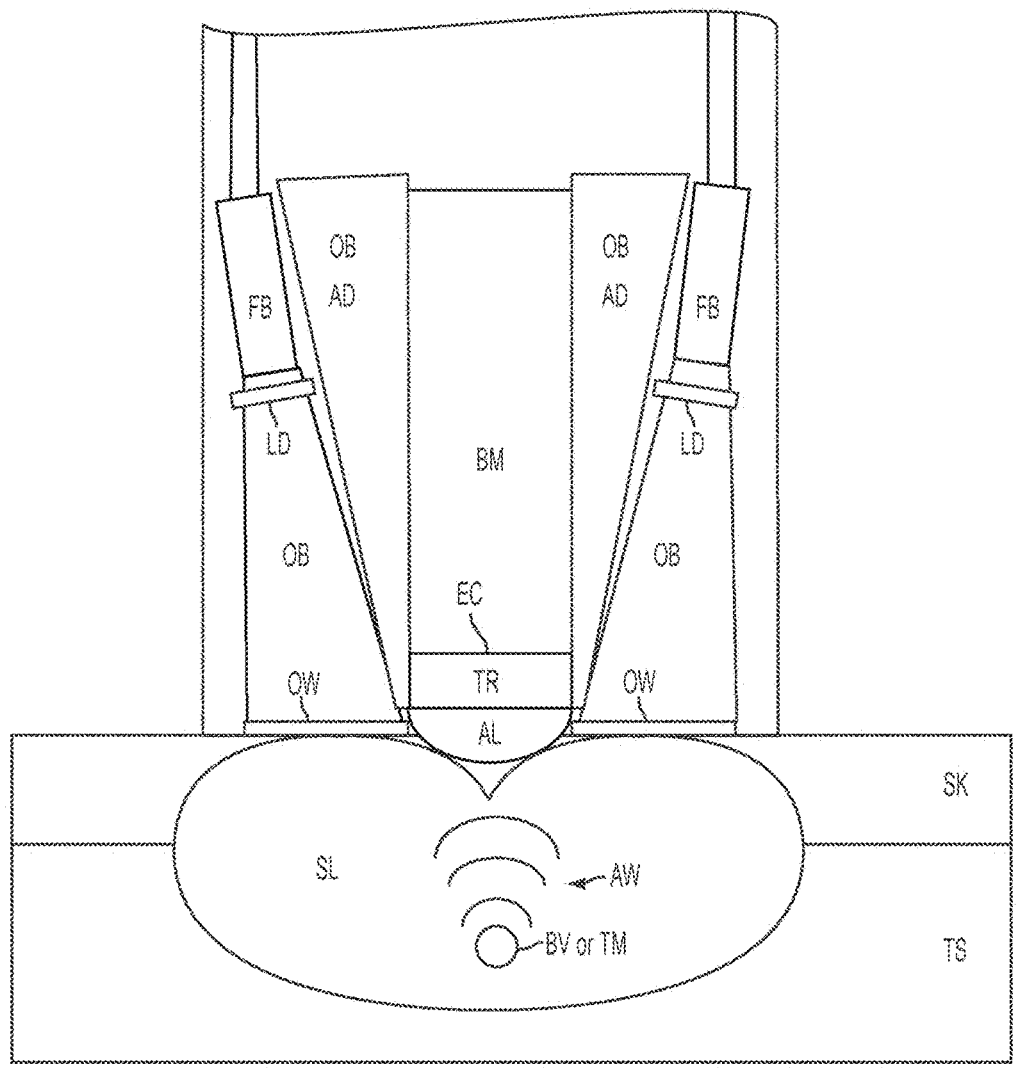
FIG. 1A illustrates an embodiment of an optoacoustic probe with illumination of tissue through skin by a scattered light beam formed in tissue by merging two optical beams.

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "an embodiment" or "the embodiment" means that a particular feature, structure, or characteristic described in connection with the embodiment is included in at least an embodiment of the disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

System Overview

In at least some embodiments, the present disclosure is directed to a dual-modality ultrasonic/optoacoustic system for medical diagnostics that uses a hand-held probe for scanning along the skin surface of an organ and provides two types of two-dimensional maps into the depth of tissue, anatomical (morphological) and functional (blood hemoglobin index and blood oxygenation index). In an embodiment, these two maps are spatially coregistered by using the same array of ultrasonic transducers and temporally coregistered by acquiring the two types of images in real time, faster than any physiological changes can occur in the tissue of diagnostic interest. The blood hemoglobin index represents blood hemoglobin concentration changes in the areas of diagnostic interest relative to the background blood concentration. The blood oxygenation index represents blood oxygenation changes in the areas of diagnostic interest relative to the background level of blood oxygenation. These coregistered maps can be used to noninvasively differentiate malignant tumors from benign lumps and cysts.

In an embodiment, the dual-modality ultrasonic/optoacoustic system of the present disclosure provides two-dimensional imaging of a body utilizing delivery of optical energy and acoustic detection of resulting transient pressure waves using interchangeable hand-held probes, one of which is flat and used to perform a translational scan through at least a flat portion of the body under examination, and the second of which is curved being shaped as a concave arc to perform a translational scan through at least a cylindrical or curved portion of the body under examination, both scans contribute to a more complete understanding normal or pathological functions in the body.

In an embodiment, at least a portion of the body under examination contain molecules of blood constituents such as hemoglobin and oxyhemoglobin responsible for body functions or receptors in cells responsible for cell functioning, water, lipids or other constituents.

In an embodiment, optical energy produced using at least one laser beam is used for body illumination with at least one wavelength of light. In an embodiment, the optical energy is pulsed, with the pulse duration shorter than the time of ultrasound propagation through the distance in the body equal to the desirable spatial resolution. In an embodiment, the optical energy is within the spectral range from 532 nm to 1064 nm. In an embodiment, the optical energy is replaced with other electromagnetic energy with the wavelength from 1 nm to 1 m.

In an embodiment, electronic signals produced by ultrasonic transducers are amplified using low noise wide band electronic amplifiers with high input impedance. In an embodiment, analog electronic signals are digitized by a multi-channel analog-to-digital converter and further processed utilizing a field programmable gate array. In an embodiment, the ultrasonic transducers are ultrawide-band transducers that detect ultrasonic signals with no or minimal reverberations. In an embodiment, the system is integrated with an ultrasound imaging system used to enhance visualization of acoustic boundaries in the body and parts of the body with different density and/or speed of sound.

In an embodiment, quantitative measurements of concentrations of target molecules, cells or tissues is made through characterization of optical energy propagation and absorption combined with processing of digital electronic signals by deconvolution of the hardware transfer function in order to obtain intrinsic optoacoustic amplitude and profile of such signals and the distribution of the optical absorption coefficient in the body.

In an embodiment, an optoacoustic contrast agent is used to visualize a portion of the body of interest or characterize distribution of certain molecules, cells or tissues in the body.

In an embodiment, the system comprises at least a laser, a light delivery system, an optoacoustic probe, an electronic system, a computer and an image display.

Laser

In an embodiment, the laser is capable of emitting short, nanosecond pulses of near infrared light at two (or more) different toggling wavelengths, i.e. two different spectral bands. In an embodiment, one of the wavelengths is preferentially absorbed by hemoglobin of blood and the other is preferentially absorbed by oxyhemoglobin of blood. In an embodiment, illumination of the organ under examination with the first laser pulse at one wavelength (spectral band) and detection of the first optoacoustic signal profile resulting from the first illumination, followed by the illumination with the second laser pulse at the second wavelength band and detecting of the second optoacoustic signal profile, can provide data that can be used for reconstruction of two coregistered tomographic images that can be used for generation of functional maps of the areas of diagnostic interest based on (i) blood hemoglobin index and (ii) blood oxygenation index.

Light Delivery System

In an embodiment, the light delivery system comprises bundles of optical fibers. In an embodiment, the input of the optical fiber bundle is circular to match the incident laser beam, while the output of the fiber bundle is rectangular to match the size and shape of the ultrasonic transducer array. In an embodiment, each fiber has a small diameter (e.g., down to 50 micron) to provide excellent flexibility of the bundles. In an embodiment, the input tip of the fiber bundle is fused to shape the bundle into a hexagon and to eliminate spaces between the fibers in the bundle, thereby providing up to 20% better transmission of the laser energy. In an embodiment, the output tip of the fiber bundle is fully randomized such that fibers that appear close to each other at the input will appear far from each other at the output or even in different branches of the bifurcated fiber bundle.

Optoacoustic Probe

The probe is designed to provide high contrast and resolution of both optoacoustic and ultrasonic images. In an embodiment, the probe is a hand-held probe with an array of ultrasonic/optoacoustic transducers, which can be designed to be single dimensional, 1.5 dimensional or two-dimensional. In an embodiment, the transducers detect acoustic waves within an ultra-wide band of ultrasonic frequencies and the ultra-wide band is shaped to match the spectrum of optoacoustic signals emitted by tissue of diagnostic interest. In an embodiment, the transducers are also designed to emit acoustic waves as short pulses of ultrasound with short ring-down time and minimal reverberations of gradually decreasing magnitude.

To achieve such a design, transducer material can be chosen from, for example, piezoelectric ceramics (such as PZT, PMN-PT, and PZNT), piezoelectric single crystals (such as PZT, PMN-PT, and PZNT), piezoelectric polymers (such as PVDF and copolymer PVDF copolymer), composite polymer-ceramic and polymer-crystal piezoelectric materials and capacitive micromachined ultrasonic transducers (CMUT). In an embodiment, the thickness of the transducer elements that provide the central frequency and materials of the backing layer and the front surface matching layer of the transducers are optimized.

In various embodiments, the shape of the ultrasound transducer array may be either flat or concave arc. A flat design is suited to scanning of the surface of an organ under examination that has radius of curvature much larger than the size of the probe, such as a human body. A concave arc-shaped design provides the largest aperture for the optoacoustic signal detection with minimal physical dimensions. The large aperture, in turn, provides for improved lateral resolution within the angle of the field of view formed by lines connecting the arc's focal point with each edge transducer of the array. The arc-shaped probe is often the most effective for scanning body surfaces that are curved with a radius approximately matching that of the probe (such as the average sized breast, neck, arms and legs).

FIG. 1A illustrates an embodiment of an optoacoustic probe that provides illumination of tissue (TS) through skin (SK) by the scattered light (SL) beam formed in tissue by merging two optical beams (OB) emerging from fiber bundles (FB) expanding and passing through light diffusers (LD) then passing through optical windows (OW). Acoustic waves (AW) generated in blood vessels or tumors (BV or TM) by the scattered light (SL) in tissue propagate through acoustic lens (AL) to transducers (TR) and converted into electrical signals being transmitted by electrical cables (EC) through the backing material (BM) to the electronic amplifiers.

In an embodiment, the design of the optical fiber bundle is as follows. The input of the fiber bundle is circular with fused fiber tips to avoid loss of light through spaces between the fibers. The fiber diameter may be approximately 200 microns for good flexibility, and a fiber diameter of 100 microns or even 50 microns may be desirable in a particular application. This fiber bundle is Y-split into two half-bundles and fully randomized, so that substantially any two neighboring fibers from the input appear in different half-bundles. At least a majority of the neighboring fibers should be randomized in this regard. Each half-bundle is preferably split into multiple sub-bundles, and each sub-bundle is placed in its slot/niche to form fiber bundle "paddles". The two paddles are placed on each side of the ultrasonic transducer (TR) array assembly. As is discussed below with reference to FIGS. 7B and 7C, the output shape of each fiber bundle paddle may be rectangular for the width of the field of view, typically 40 mm, and have triangular shaped ends. Such triangular shape allows the output beam to have smooth edges after passing through light diffuser (LD), FIG. 1A. Finally, the optical beam from fiber bundle paddles exit from the probe into the skin (SK) through optical windows (OW) that comprise thin anti-reflection-coated glass plates or anti-reflection-coated polymer or plastic plates with acoustic impedance matching that of tissues to be imaged.

There are a number of objectives for the present optoacoustic probe design: (i) substantially no light should propagate either through the acoustic lens (AL) or through the optical block acoustic damper (OBAD) on the sides of the probe, (ii) substantially no acoustic waves should be generated in the acoustic lens or the optical block acoustic damper materials through absorption of light; acoustic waves in a wide range of ultrasonic frequencies from 0.1 MHz to 15 MHz should be able to pass through (AL) with no attenuation, and no acoustic waves should be able to pass through OBAD; (iii) the optical beams (OB) exiting through optical windows (OW) should have smooth edges of the optical fluence, and these optical beams should enter the skin as close to each other as necessary to merge due to optical scattering within the skin and enter underlying tissue under the array or transducers providing maximum fluence in the image plane.

In an embodiment, the light delivery system directs light underneath the transducer elements, not through the array of transducer elements. In an embodiment, the design of the optoacoustic probe is based on an array of ultrasonic transducers with fiber optic delivery systems on each side of the ultrasonic array, positioned as close to the transducers as possible and with dimensions in the elevation axis of the transducer as small a possible, considering the need to focus ultrasonic beams to the depth of the most probable target. In an embodiment, the fiber optic delivery system is designed to allow penetration of the optical energy of the near infrared light into the organ being imaged, such as a breast, and minimum opto-thermo-mechanical interaction of the light beam with skin.

Another alternative design of the light delivery system delivers light to a mirror or prism(s) placed underneath of the ultrasonic transducers in order to reflect the light orthogonally to the skin surface of an organ being imaged. In such embodiments, a standoff can be placed between the transducer elements and the skin/tissue. These alternative embodiments may be combined within the scope of the invention.

Detailed Description of Aspects of System Components

Optical Illumination and Probe Design

An acoustic lens is typically placed on transducers within an optoacoustic probe for purposes of focusing ultrasonic beams. While a probe could be provided without an acoustic lens, if there is no lens then ultrasonic transducers may be directly exposed to light and absorb such light, which can result in very large artifact ultrasonic signals, especially where such light is pulsed. Optical illumination of the lens on an ultrasonic probe causes very strong transient acoustic waves that result in image artifacts. Up to 50% of near infrared light can be diffusely scattered by skin, depending on skin color. Mismatch of acoustic impedance between the lens of the transducer elements can cause reverberations with long ring down time. Therefore, an embodiment of a probe design includes a white strongly scattering opaque lens. If such lens is not needed due to curved shape of each transducer element, then a white strongly scattering front matching layer should be employed to protect transducer elements from near-infrared light.

Figure 1B:
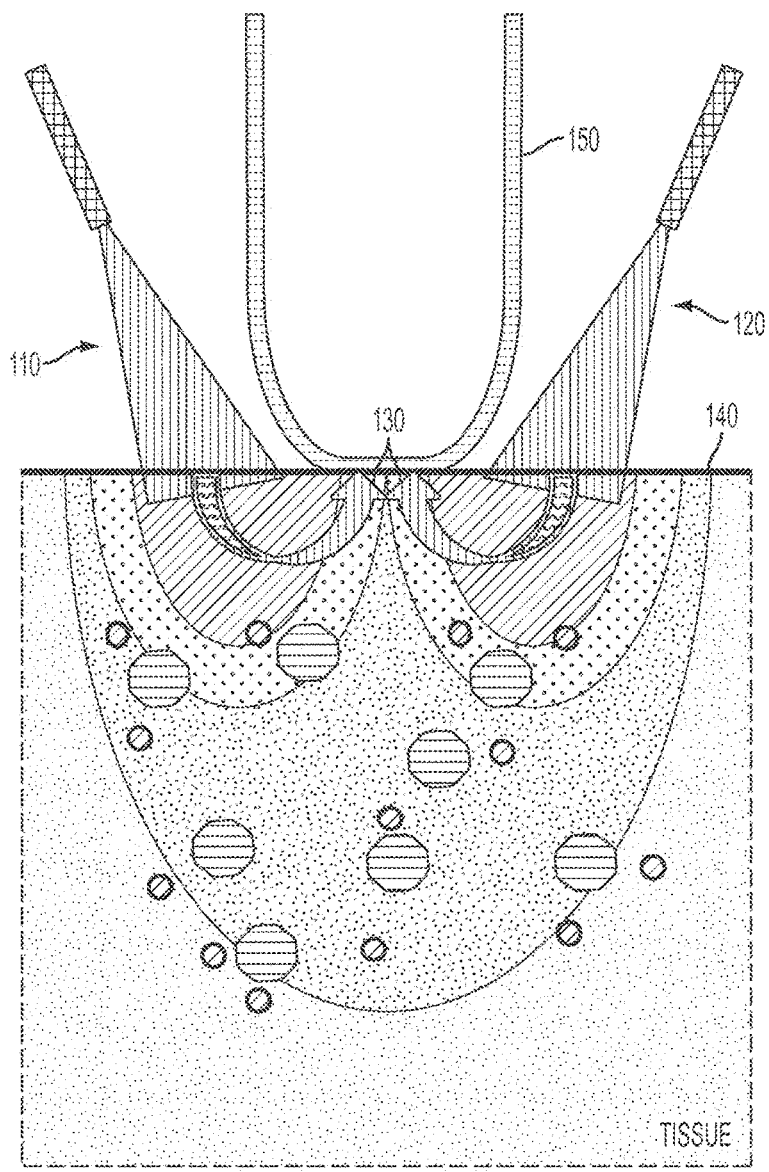
FIG. 1B illustrates how laser illumination light and an acoustic signal from an optoacoustic probe can be scattered from the skin towards an acoustic lens of a probe.

FIG. 1B illustrates how laser illumination light 110 and 120 from an optoacoustic probe can be scattered 130 from the skin 140 towards an acoustic lens 150 of a probe.

Furthermore, (laser) optical pulses can have a direct impact on ultrasonic transducers of the acoustic waves induced by strong interaction of the optical pulses with skin of the organ being imaged that laterally traverse along the skin surface in a direction orthogonal to the image plane. When detected by the array of transducers, spatial distributions of these acoustic waves are projected onto the optoacoustic image at a depth equal to the lateral distance between the array of transducers and the optical beams on the skin surface, creating artifacts. Furthermore, acoustic waves generated in skin through reverberation of the acoustic lens and the housing of the probe can further affect the quality of imaging.

Figure 2A:
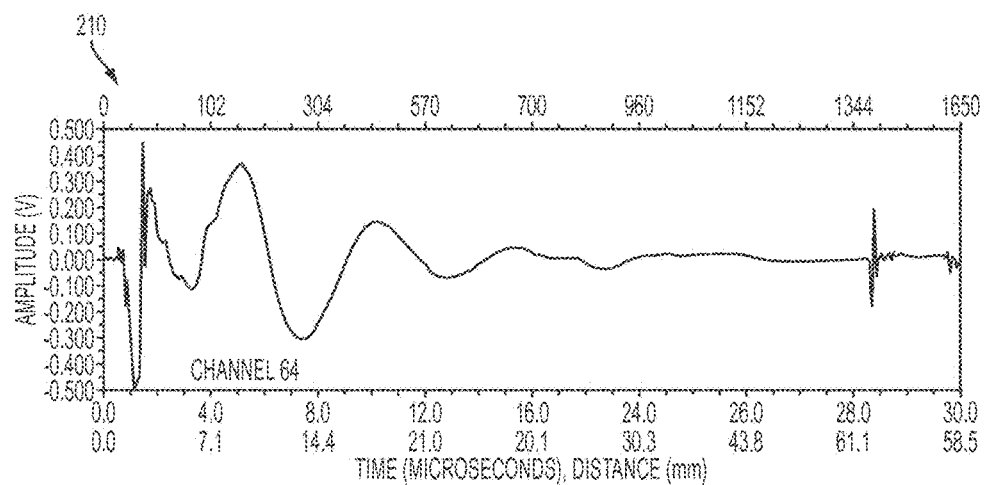
FIGS. 2A and 2B illustrate optoacoustic signals showing the impact of lateral ultrasonic waves induced by laser pulses in skin using optical beams on each side of an ultrasound transducer array, and using detection by transducers tilted at large angle relative to the plane of images generated therefrom.
Figure 2B:
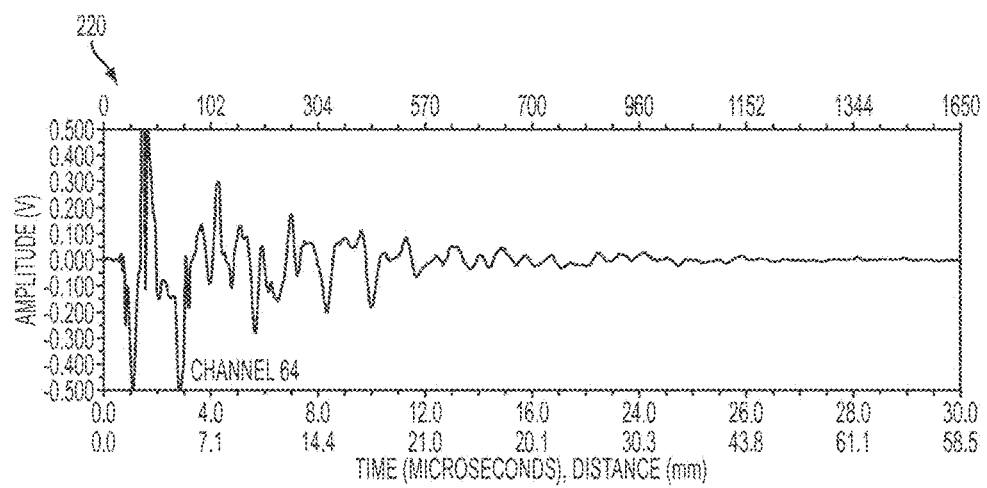

FIGS. 2A and 2B illustrate exemplary optoacoustic signals showing impact of lateral ultrasonic waves induced by laser pulses in skin using optical beams on each side of an ultrasound transducer array. The signals shown are generated by transducers in the direction almost orthogonal to the plane of images generated therefrom. Such transducers may receive signals at large oblique angle (up to 90 deg) relative to the plane of images generated therefrom, which is undesirable. Therefore, the design of the transducer array includes means to reject signals coming out of the image plane. Such means include but not limited to concave arc shape of the transducer elements and acoustic lens and delivery of the optical beam underneath the transducers. The detected optoacoustic signals 210 in FIG. 2A were generated using an effective acoustic coupling agent, in this case water. The signals 220 in FIG. 2B were generated in the absences of such acoustic coupling agent, i.e., using only air space to couple the acoustic signals to the transducer array.

Furthermore, the finite dimensions of the optical beam can affect the acoustic waves generated in response to impingement of the optical beam on tissue. Such acoustic waves can be generated at the sharp edges of the optical beam, propagate towards the array of transducers and result in artifacts. Since a system that utilizes flat linear array of ultrasonic transducers is configured such that the first and the last transducer in the array detect these waves first and the central transducers detect these waves the last, this "edge effect" results in v-shaped artifacts on a sinogram of optoacoustic signals and low frequency bulk artifacts on optoacoustic images.

Figure 3:
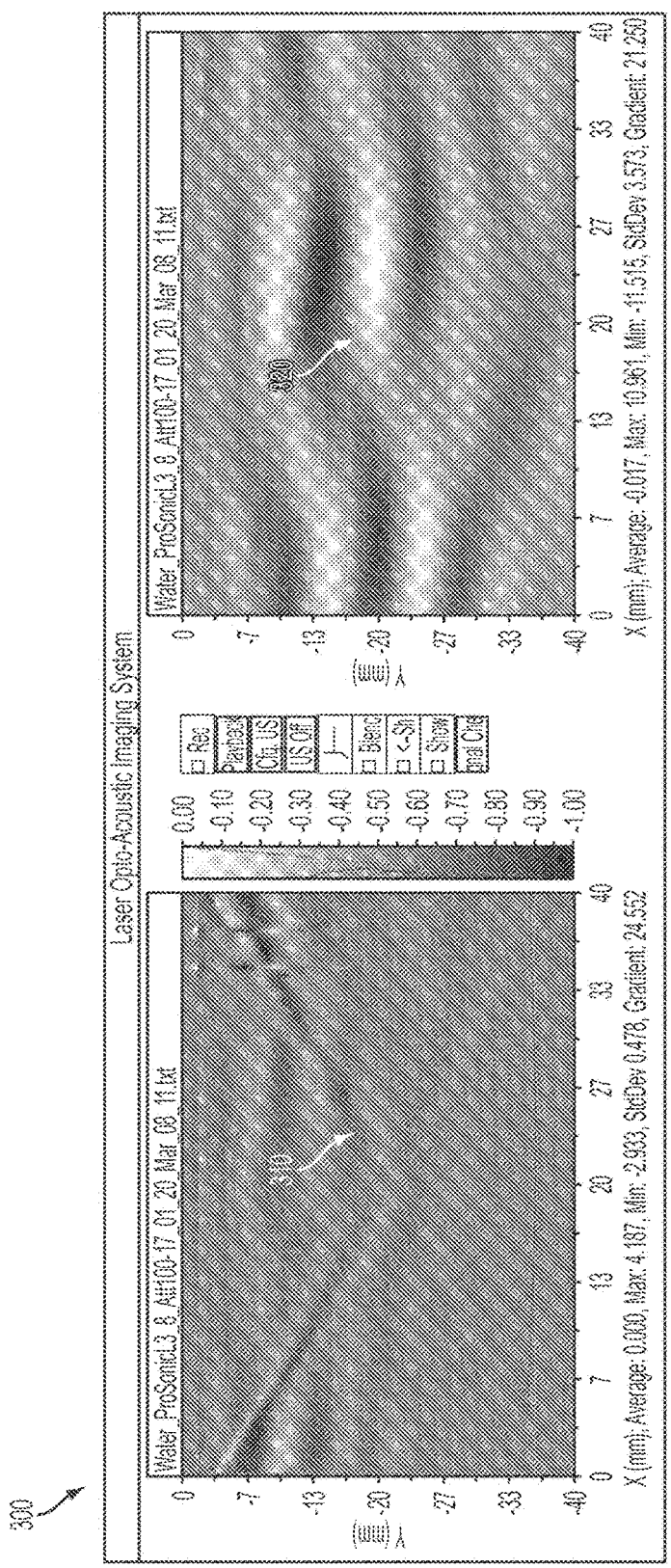
FIG. 3 illustrates an embodiment of manifestation of image artifacts associated with the edge effect of optical illumination beam having abrupt changes of the optical fluence.

FIG. 3 illustrates an example of manifestation of v-shaped artifacts 310 on a sinogram 300 of optoacoustic signals and associated artifacts 320 on optoacoustic images. Since these acoustic waves are associated with the edge effect of the optical illumination beams having abrupt changes of the optical fluence, in an embodiment, one can see a V-shaped bright signals on the sinogram and associated series of artifact waves on the opto-acoustic image.

Furthermore, the illumination geometry of optical beams projected by an optoacoustic probe can affect image quality. Where the optical beams of an optoacoustic probe are placed too far apart, this can result in a gradual transition from the dark field illumination (two separate optical beams on each side of the probe resulting in the absence of direct light under the probe in the image plane) into the bright field of illumination (one beam under the probe going into the depth of tissue along the image plane). This transition creates a problem in the image brightness map making the map not quantitatively accurate and causes artifacts at the depth equal to the initial width between separate optical illumination beams on each side of the probe.

FIGS. 4A-4C illustrate an embodiment wherein optical illumination of tissue is accomplished using a hand-held optoacoustic probe 410, 420, 430 that delivers optical energy from either under the optoacoustic probe or on the side of the probe at different distances. In the embodiment of FIG. 4A, when the optical beams are delivered under the ultrasonic probe, the distribution of the optical energy in the image plane has a smooth gradient with a maximum at the skin surface. This optical distribution is beneficial for high contrast of optoacoustic images. In the embodiment of FIG. 4B, when the optical beams are delivered close to a thin optoacoustic probe, the two beams can merge due to optical scattering within the skin, so that the distribution of the optical energy in tissue under the skin can be made similar to the embodiment of FIG. 4A. In the embodiment of FIG. 4C, when the optical beams are separated by a large distance, they merge only at significant depth within tissue, creating the optical distribution in the image plane with a dark zone (no light) in a subsurface layer of the tissue and a bright zone in the depth of the tissue, which is detrimental to the contrast of optoacoustic images, especially considering projection of brightly illuminated areas of skin onto the optoacoustic image plane at a depth equal to the separation distance of the two beams.

Thus, in the embodiments illustrated in FIGS. 4A-4C, the image brightness map 412, 422 and 432 of the tissue being scanned is optimized where the illumination of the skin is directly under the probe 410. As the distance between the center of the transducers and the center of the optical beams increases, as shown at 420 and 430, the image brightness map 422 and 432 of the tissue being scanned becomes progressively more uneven.

Lastly, the reflection from boundaries of tissue structures (such as tumor, vessels or tissue layers) of laser-induced ultrasound waves launched into the tissue after being generated in skin, can also lead to image artifacts represented by lines, curves and overall noise.

In an embodiment, the acoustic lens of the probe is designed such that the lens reflects and scatters, but does not absorb, light from the illumination components, yet it is optically opaque. In various embodiments, such lens can be made either using strongly optically scattering material such as silicon rubber filled with titanium dioxide or barium sulfate powder, or using a thin metallic highly reflective layer such as aluminum or gold or a combination a white opaque lens material and a metal layer. In an embodiment, to avoid peel-off of the thin metallic layer from the front surface of the acoustic lens, in case of a combination of diffusely scattering material of the lens and a thin reflective layer (foil), the metallic reflective layer can be placed between the two layers of diffusely scattering material. As it is difficult to make a material with absolutely zero optical absorption, and such absorption may generate ultrasound in thermoelastic materials, the lens material can be made from thermoplastic materials having minimal thermal expansion, which produces minimal or no ultrasound in response to the absorbed optical energy.

Figure 5A:
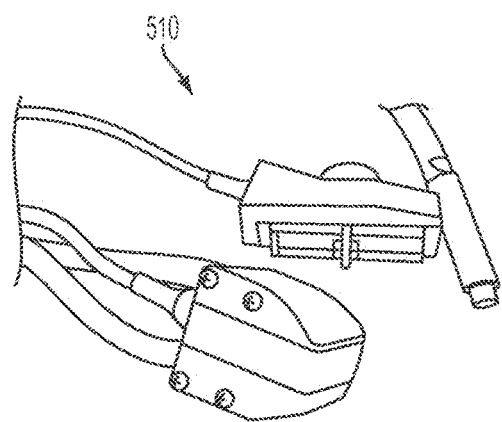
FIGS. 5A and 5B illustrate two embodiments of a hand-held optoacoustic ultrasonic probe protected from optical illumination of the acoustic lens.
Figure 5B:
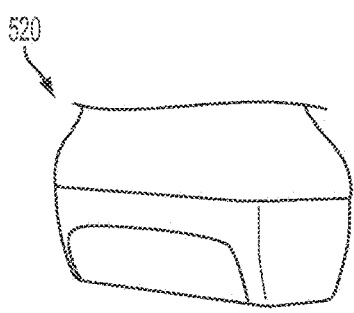

FIGS. 5A and 5B illustrate two embodiments, respectively, of hand-held optoacoustic ultrasonic probes 510 and 520 that are protected from optical illumination of the acoustic lens. In FIG. 5A, a totally reflective opaque white lens is utilized, and in FIG. 5B a partially reflective white lens is utilized, with light reflection capability of the lens enhanced by a gold layer or coating.

Figure 6:
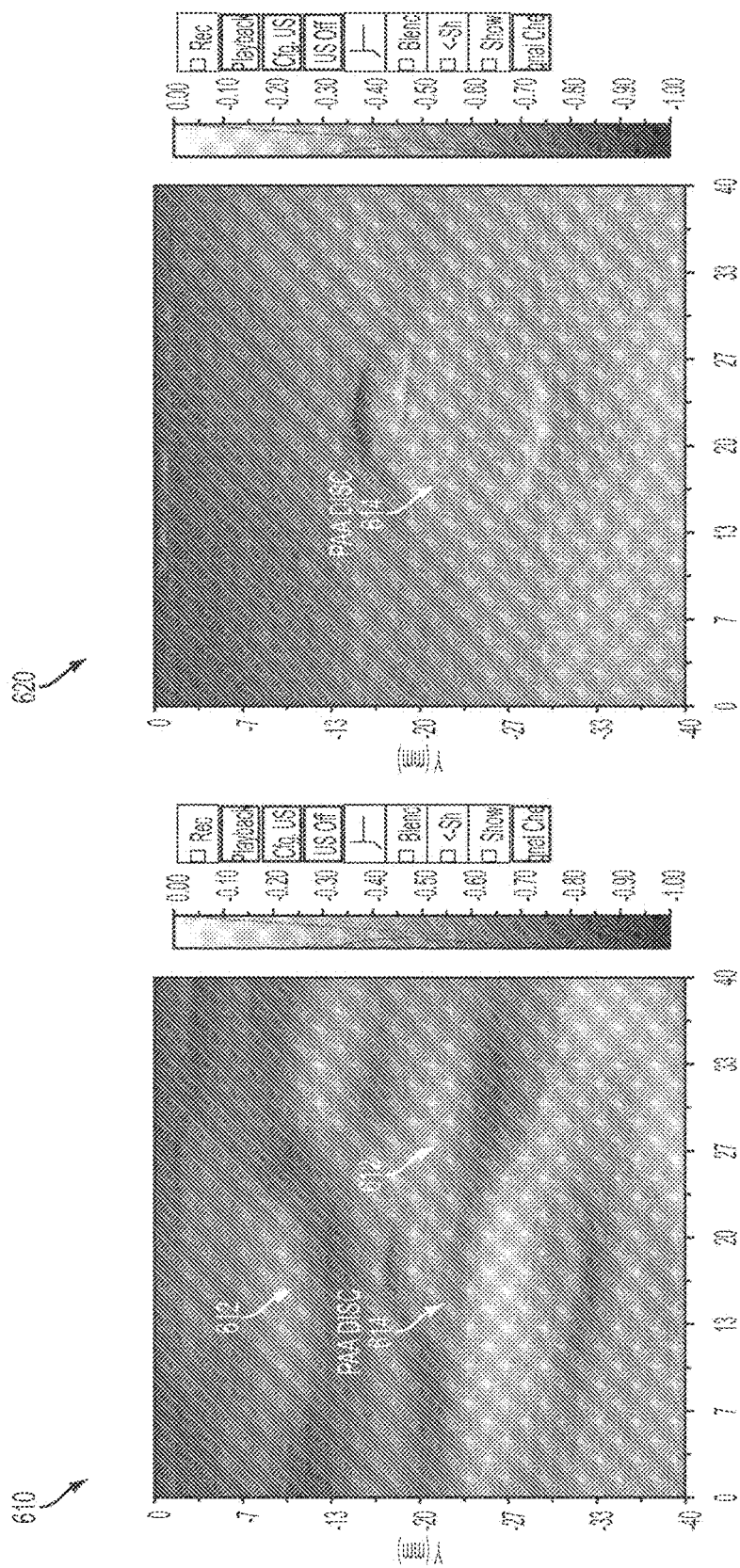
FIG. 6 illustrates optoacoustic images using a probe with an acoustic lens that is not totally optically reflective and with a probe having an optically reflective layer of gold, which removes lens related image artifacts.

FIG. 6 illustrates optoacoustic images using a probe with a non-reflective acoustic lens 610 and a probe with reflective layer of gold 620. The probe utilizing a reflective layer of gold 620 produces an image with reduced artifacts 612 and 614.

In an embodiment, the probe housing serves as hypoechoic encapsulation of the probe, which means that the probe housing is made from materials that (i) do not absorb laser light (more specifically near-infrared light), but if a small absorption is unavoidable, the materials having low thermal expansion do not emit ultrasound after absorption of the laser light, (ii) strongly attenuate and dampen ultrasonic waves and do not reverberate. The transducer assembly inside the probe housing is also made of the hypo-echoic material. Alternatively, a layer of said hypo-echoic material is placed between the transducer assembly and the fiberoptic assembly to avoid generation of any ultrasound upon interaction of light with transducer assembly. In various embodiments, such materials can be chosen, for example, from white color porous and anechoic heterogeneous composites for baffles, foams, polymers, rubbers and plastics (such as CR-600 casting resin available from Micro-Mark of Berkeley Heights, N.J., or AM-37 available from Syntech Materials of Springfield, Va.), and others. In an embodiment, any such materials are electrically non-conducting insulators to, inter alia, protect the probe from external electromagnetic emissions.

In an embodiment, the optical illumination subsystem is configured to deliver optical beams with smooth intensity edges. In an embodiment, the width of the optical beams is equal to that of the array of ultrasonic transducers within the optoacoustic probe (for example, about 5 mm). This is achieved by designing the bundle of optical fibers to have a gradually decreasing density of fibers at the edges. This design enables one to deliver laser illumination to the skin of the organ under examination so that the beam does not generate sharp edge-related acoustic waves, and such laser-induced acoustic waves do not produce V-shaped artifacts in the sinogram of optoacoustic images.

Figure 7A:
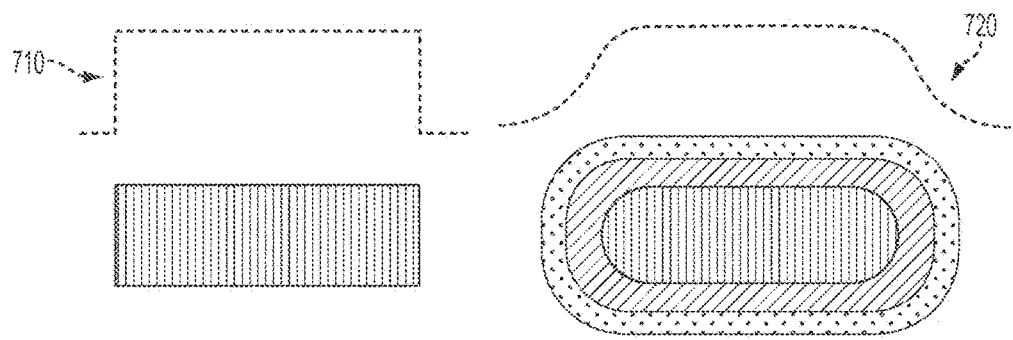
FIG. 7A illustrates an embodiment of an optical beam with sharp edges that may produce edge effects of acoustic waves and related artifacts and an optical beam with smooth edges producing reduced edge-related artifacts.
Figure 7B:
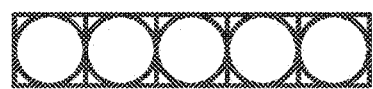
FIGS. 7B and 7C illustrate output fiber bundle designs shaped to provide even illumination of the image plane and reduce edge related optoacoustic artifacts.
Figure 7C:
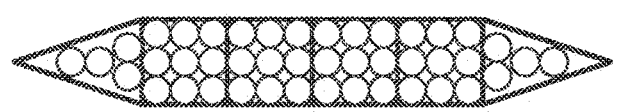

FIG. 7A illustrates an embodiment of an optical beam with sharp edges 710 that may produce edge effects of acoustic waves and related artifacts and an optical beam 720 with smooth edges producing reduced edge-related artifacts. FIGS. 7B and 7C illustrate that an optical beam with smooth edges of fluence can be produced using a fiberoptic bundle design having multiple sub-bundles and a triangular shape in each end of the fiber bundle assembly.

In an embodiment, the fiber bundle is positioned at a distance from skin that is sufficient for the optical beam to expand to a desirable width. Where the dimensions of the probe are compact, the fibers used in the fiber bundle can be selected to have a higher numerical aperture (e.g., >0.22). In an embodiment, in order to achieve better coupling of the optical beam into the skin, the beam is delivered through an optical window. In such embodiment, the optical window touches the skin, making its surface flat for better light penetration, simultaneously removing any excess of coupling gel from the skin surface being imaged. In an embodiment, the fiber bundle and the optical window are incorporated into the probe housing, so that the air gap between the fiber bundle and the window is protected.

In an embodiment, the optical window is designed is to allow minimal interactions of both the optical beam and the laser-induced acoustic waves with such window. In an embodiment, the window is very thin and made of optically transparent material with antireflection (AR) optical coating. In an embodiment, such material has anechoic acoustic properties. These anechoic acoustic properties and the fact that the illuminated skin is being depressed upon optoacoustic scanning results in dampening of ultrasonic waves laterally propagating from the laser-illuminated skin surface to the transducer array, thereby reducing associated artifacts.

In an embodiment, the probe is designed such that the optical beams are very close to the transducer elements on each side of the ultrasonic probe, which is made as thin as technologically possible. In an embodiment, the thickness of the probe is so small (e.g., 5 mm) that the light beams delivered to skin at this distance, d, from the probe center will merge into one beam within the thickness of the skin (about z=5 mm), and the tissue of the organ under examination receives one beam underneath the transducer elements. This is called bright field illumination. In an embodiment, the optoacoustic probe is designed such that the optical light beam is delivered to the skin directly underneath the transducer elements.

Figure 8:
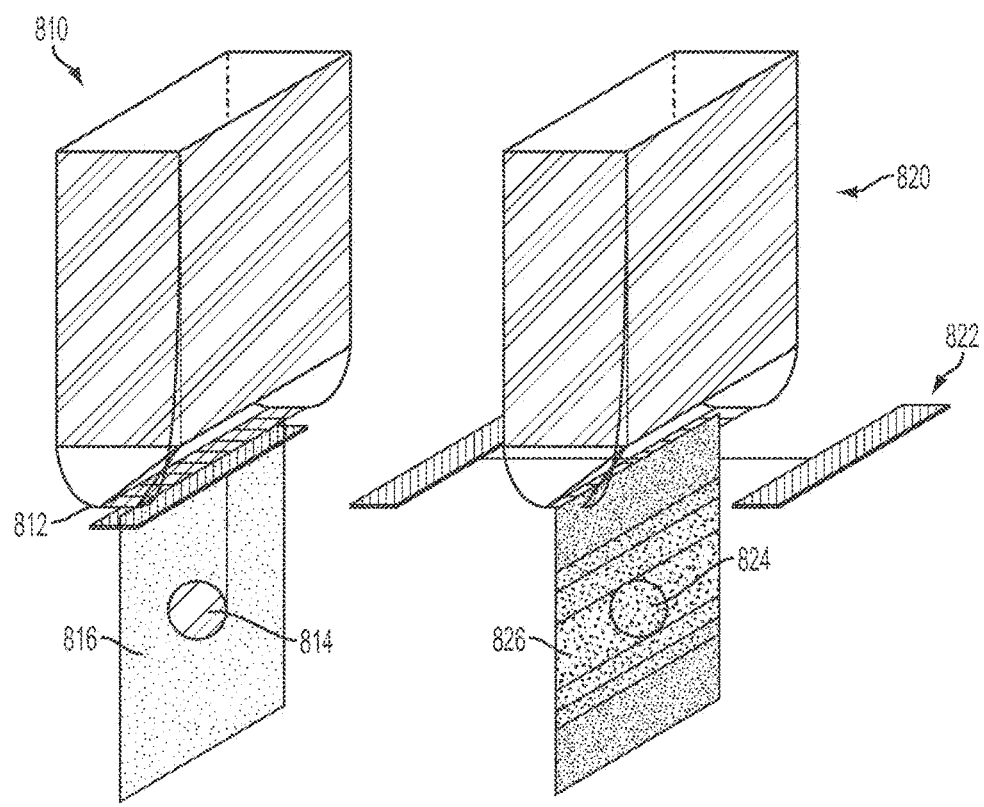
FIG. 8 illustrates the effect of optical illumination for two probes where two fiber bundles on each side of the respective probes are oriented to illuminate skin directly under the probe.

FIG. 8 illustrates the effect of optical illumination for two probes 810 and 820 where two fiber bundles on each side of the respective probes are oriented to illuminate skin directly under the probe 812 and on either side of the probe 822. Where the skin is illuminated directly under the probe 812, a tumor 814 is clearly discernable and there is no clutter on the image background 816. Where the skin is illuminated on either side of the probe 822, the tumor is not discernable 824 and there are numerous artifacts on the image background 826.

In an embodiment, the optical beam width is designed to deliver increased light into the slice of tissue being imaged. In an embodiment, the beam is homogeneous, such that it has a constant fluence through the beam, as a heterogeneous beam generates acoustic sources of heterogeneities, which in turn produce artifacts in optoacoustic images. The fluence level is defined by the ANSI laser safety standards for the laser illumination of skin. The beam width is limited by the capability of the optical scattering in tissue to deliver photons of light into the central slice located underneath the transducer elements (the slice being imaged). In an embodiment, the length of the optical beam is equal to the length of the transducer array. In an embodiment, the optical beam also has smooth edges, that is to say, gradually reduced fluence at the edges, since sharp edges produce strong edge artifacts on optoacoustic images.

In an embodiment, design features of the optical illumination system and optoacoustic probe of the present disclosure can be summarized in the following Table:

TABLE 1

Summary of optical illumination and probe design.

| System Feature | Advantages |
| --- | --- |
| Arc hand-held probe | Higher aperture - lower distortions |
| Light delivery into the imaging plane | Improves optoacoustic image contrast and decreases artifacts by increasing the ratio of useful information (from the imaging plane) to noise (outside of the imaging plane) |
| Optical shielding of the probe | Reduces artifacts from direct and scattered light striking the acoustic lens, probe housing, etc. |
| Acoustic shielding of the probe | Acoustic shielding of the probe's housing reduces artifacts (clutter) from acoustic waves propagating through the probe's housing |
| Using ultrawide band transducers for both ultrasound and optoacoustic imaging | Allows to have the same array working in ultrasonic and optoacoustic imaging |

In various embodiments, the shape of the ultrasonic transducer array for the combined optoacoustic/ultrasonic imaging can be either flat or convex arc-shaped. In an embodiment, the probe shape for optoacoustic imaging is concave arc-shaped. Such a concave shape provides a large aperture with minimal physical dimensions, wider field of view of an object being imaged, which in turn provides for improved lateral resolution and better reconstruction of the shape of the object being imaged.

Figure 9A:
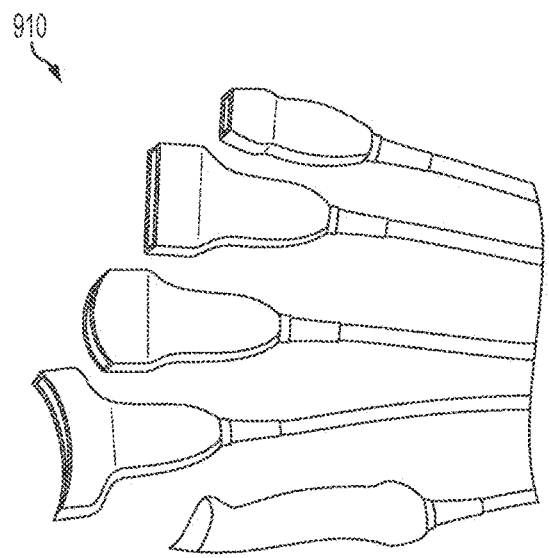
FIG. 9A illustrates embodiments of ultrasonic probes having flat, concave or convex arc shapes.
Figure 9B:
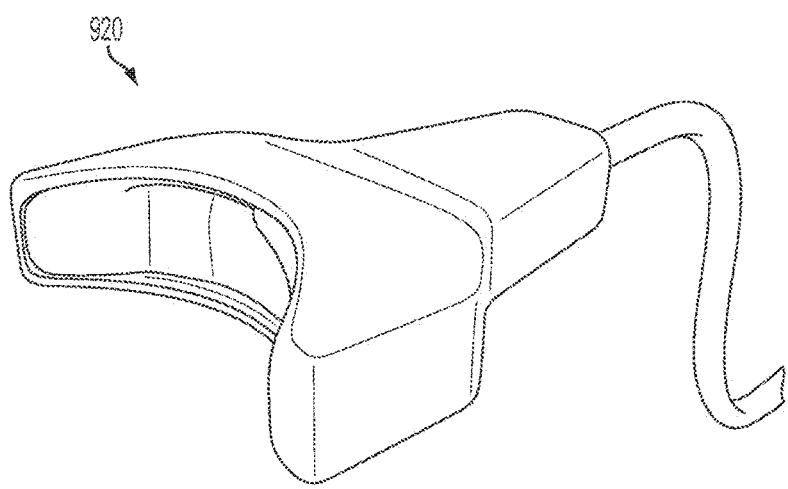
FIG. 9B shows a hand-held optoacoustic probe having a concave arc shape.
Figure 9C:
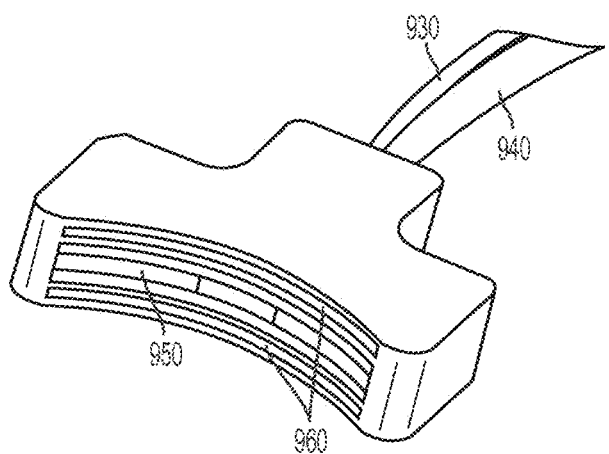
FIG. 9C illustrates details of a hand-held optoacoustic probe having a concave arc shape.

FIGS. 9A-9C illustrate embodiments of optoacoustic/ultrasonic hand-held probes having flat or concave arc shapes 910 (FIG. 9A) and a hand-held optoacoustic probe with a concave arc shape 920 (FIG. 9B). FIG. 9C illustrates details of the optoacoustic/ultrasonic hand-held probe design with its face showing ultrasonic transducers assembly, two layers of hypo-echoic light reflecting and ultrasound damping material on each side, and two optical windows for delivery of the optical beam.

FIG. 9C illustrates details of a hand-held optoacoustic probe having a concave arc shape. Electrical cables 930 are provided for bi-directional communication to and from the probe, and fiberoptic bundles 940 are provided for delivering light to the probe. An array of wide-band ultrasonic transducers 950 send and receive acoustic energy. The transducer array 950 is covered by an opaque white cylindrical lens (not shown for clarity purposes) that extensively scatters and reflects near-infrared light. Optical windows 960 provide optical beam outputs. In the embodiment FIG. 9C, the ultrasonic transducers within the probe may be designed so as not to be sensitive to lateral acoustic (ultrasonic) waves and to be free of reverberations, especially in the lateral direction. This can be achieved by the selection of the piezoelectric composite material, the shape of piezoceramic elements in the matrix and anechoic properties of the matrix. In an embodiment, the ultrasonic transducers are also designed to possess high sensitivity within an ultrawide band of ultrasonic frequencies. This in turn results in minimal reverberations that cause artifacts on optoacoustic/ ultrasonic images.

Figure 9D:
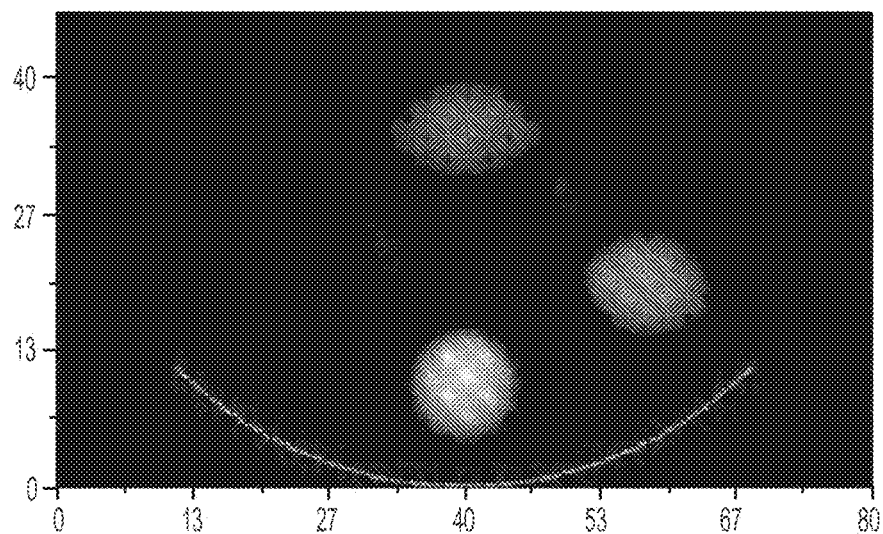
FIG. 9D shows an optoacoustic image of three spherical objects and demonstrates that within the field of view of the arc spatial (and especially lateral) resolution is excellent even for a large object.

FIG. 9D shows an optoacoustic image that illustrates advantages of the concave-arc shaped hand-held probe in terms of resolution in optoacoustic images. As presented in this embodiment, the shape and sharp edges of a large sphere are well depicted in cases where the object is within the field of view of the probe aperture. Outside the probe aperture resolution and accuracy of shape reproduction decreases, however remains better than those for flat linear probes of similar width.

Figure 9E:
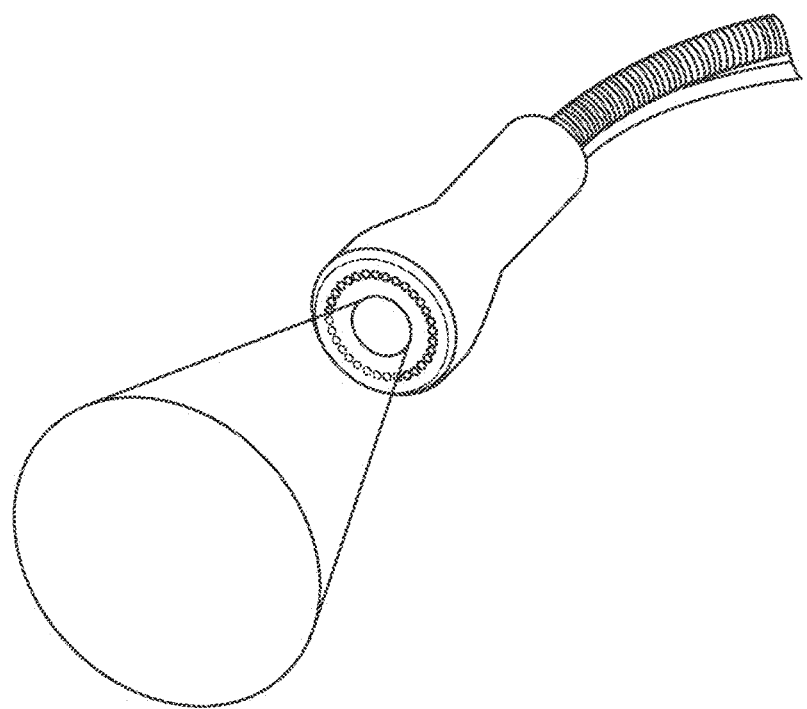
FIG. 9E illustrates an alternate embodiment of an optoacoustic/ultrasonic hand-held probe design.

FIG. 9E illustrates an alternate embodiment of an optoacoustic/ultrasonic hand-held probe design that is capable of two-dimensional imaging within the plane going parallel to the skin surface at various selected depths, and three-dimensional images as well.

In an embodiment, a hand-held probe that is scanned along the skin surface producing real-time two-dimensional images of tissues in the body under examination also has a component serving for accurate global 3D positioning of the probe. This design allows the imaging system to remember positions of all tissue slices and to reconstruct three-dimensional images at the end of the scanning procedure.

Electronic Data Acquisition System

In an embodiment, the present disclosure is directed to an optoacoustic imaging system having an electronic data acquisition system that operates in both optoacoustic and ultrasonic modes and can rapidly switch between such modes. In an embodiment, this is achieved with firmware that controls functions of a Field Programmable Gate Array (FPGA), the main microprocessor on the electronic data acquisition system. In an embodiment, a reprogrammable FPGA can toggle between optoacoustic and ultrasound operation modes in real-time, thus enabling co-registration of ultrasound and optoacoustic images, which can be used for diagnostic imaging based on functional and anatomical maps. In an embodiment, FPGA functions include controlling, acquiring, and storing optoacoustic and/or ultrasound data, signal processing and transferring data for real-time image reconstruction and processing. In an embodiment, the FPGA may also be employed in ultrasound beam forming and image reconstruction.

In an embodiment, the electronic data acquisition system design utilizes one or more multi-core Graphical Processor Units (GPU) for image reconstruction and processing. In the ultrasound mode, in an embodiment, the FPGA controls the ultrasound transmission and it performs both ultrasound and optoacoustic data acquisitions on a multi-channel board. In order to enhance operation of the memory of the FPGA, an external memory buffer can be used. In an embodiment, the FPGA allows rapid reprogramming of ultrasonic data acquisition with signal/frame repetition rate of about 2 to 20 kHz to optoacoustic data acquisition with signal/frame repetition rate of about 10-20 Hz, and also configures the structure of gates and internal memory structure and size to allow real-time switching between ultrasound emission and detection, laser synchronization, and system controls. In an embodiment, multiple FPGAs can be used to enhance the system performance. In an embodiment, in the ultrasound and optoacoustic modes, the FPGA clock can be changed by the appropriate time-division multiplexing (TDM). In an embodiment, the design of a multi-channel electronic data acquisition system can be based on modules, with a module typically being from 16 to 128 channels, although 256 channels or more may be appropriate in some applications. In an embodiment, the design of a multi-channel electronic data acquisition system has 64 channels.

In order to achieve dual modality operation of the optoacoustic/ultrasonic system, a separate optoacoustic electronic system could also be combined with a separate ultrasonic electronic system through a single probe. In an embodiment, the probe has a cable that has a Y-split to connect the probe to optoacoustic and ultrasonic electronic systems. In an embodiment, a programmable electronic switch allows one to send the detected signal from the probe (transducer array) either to the optoacoustic electronics (to operate in optoacoustic mode) or to the ultrasonic electronics and from the ultrasonic electronics to the probe (to operate in ultrasound mode). In an embodiment, a synchronization trigger signal is sent to the optoacoustic and ultrasonic systems sequentially, so that the optoacoustic and ultrasonic images are acquired one after the other.

Processing, Reconstruction and Display of Images

Signal Processing

In various embodiments, a goal of the diagnostic imaging procedure is to display each pixel with a brightness that correctly replicates the originally generated signals in each voxel of tissue displayed on the image. On the other hand, intrinsic pressure signals generated by optical pulses within tissues may be significantly altered in the course of propagation through tissue and especially in the course of detection and recording by the ultrasonic transducers and the electronics subsystem.

In an embodiment, detected signals are processed to reverse alterations and restore original signals. In an embodiment, such reversal can be achieved through deconvolution of the impulse response (IR) of the system. In an embodiment, the impulse response can be measured by recording and digitizing a delta-function ultrasonic signal generated by short (nanosecond) laser pulses in a strongly absorbing optical medium with high thermoelastic expansion coefficient.

One component of the impulse response is the acoustoelectrical impulse response, which provides for the optoacoustic or ultrasonic signal distortions due to the properties of the ultrasonic transducers, cables and analog electronics. A second part of the impulse response is the spatial impulse response that provides for the signal distortions associated with finite dimensions of the ultrasonic transducers. In various embodiments, large transducers can integrate ultrasonic waves incident at an angle, whereas point-source-like transducers can provide perfect or near perfect delta-function spatial impulse response.

In an embodiment, any distortions in acousto-electrical impulse response can be reversed by the impulse response deconvolution from the detected signals. However, possible distortions in the spatial impulse response can be avoided by designing transducers with small dimensions within the image plane. In an embodiment, the dimensions of the transducers are much smaller than the shortest wavelength of the ultrasound that may be detected or emitted by the transducers.

Figure 10A:
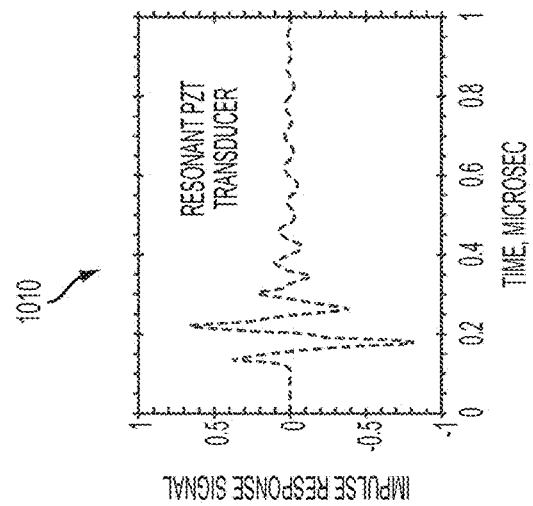
FIGS. 10A-10C show examples of the impulse response of an ultrasonic transducer with a relatively narrow ultrasonic frequency band of sensitivity, the impulse response of an ultrawide-band ultrasonic transducer, and the ultrasonic spectra of transducer sensitivity as a function of frequency for ultrawide-band and narrow band resonant transducers.
Figure 10B:
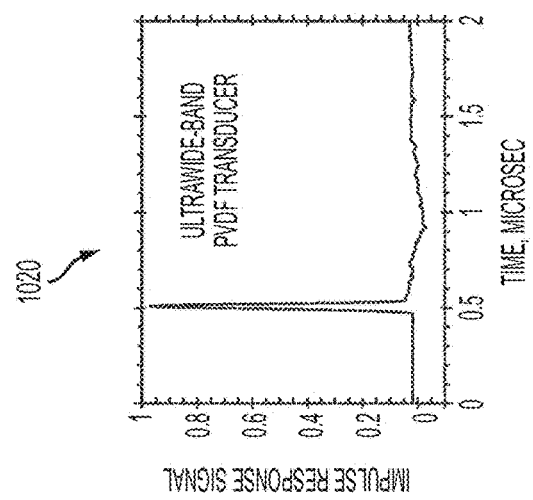
Figure 10C:
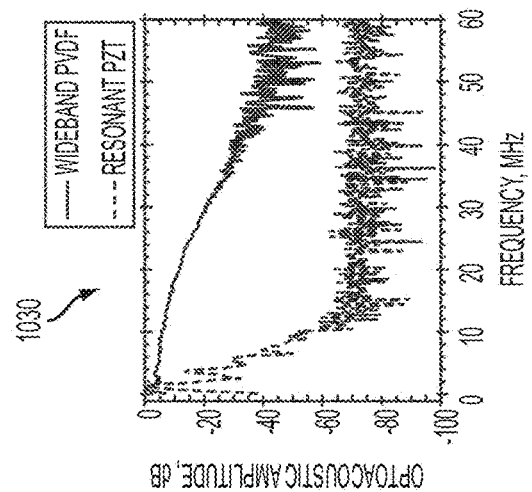

FIGS. 10A-10C show examples of the impulse response of an ultrasonic transducer with a relatively narrow band of sensitivity 1010, the impulse response of an ultrawide-band ultrasonic transducer 1020 and ultrasonic spectra of the transducer sensitivity as a function of frequency for ultrawide-band and narrow band resonant transducers 1030.

In an embodiment, the first step in processing an optoacoustic signal in an imaging system that produces two-dimensional optoacoustic images is deconvolution of the acousto-electrical impulse response.

Figure 11B:
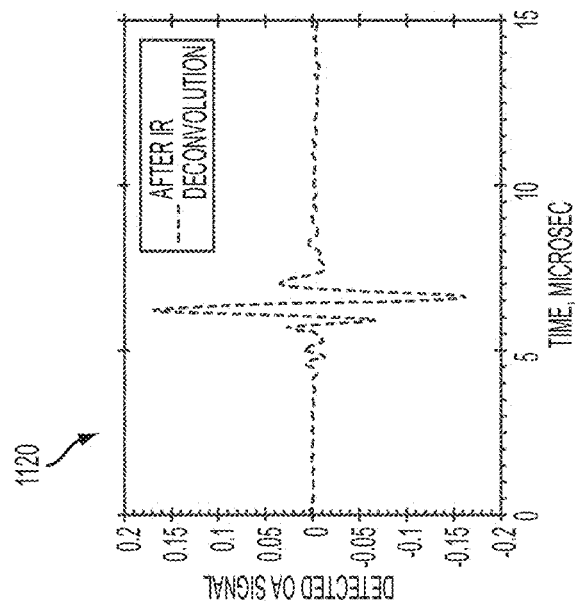
FIGS. 11A-11B provides an illustrative example of the deconvolution of impulse response of transducers from the detected optoacoustic signals where deconvolution restores the original, unaltered, N-shaped pressure signals.
Figure 11A:
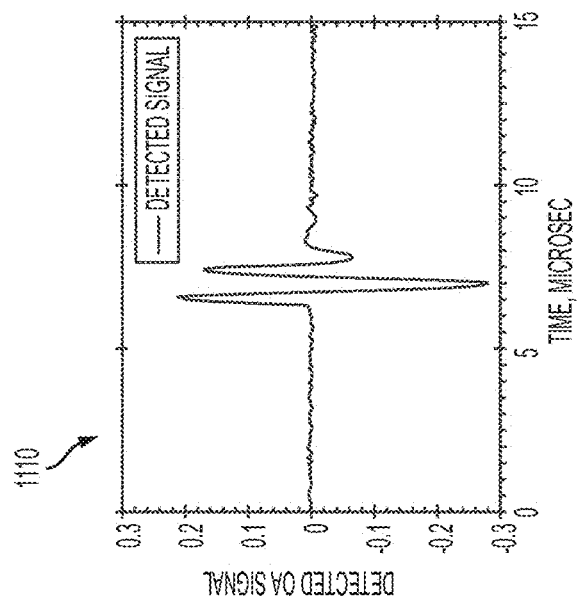

FIGS. 11A and 11B provide an illustrative example of the deconvolution of impulse response of transducers from the detected optoacoustic signals 1110, where deconvolution restores the original, unaltered, N-shaped pressure signals 1120.

In an embodiment, the second step in processing an optoacoustic signal is signal filtering to remove noise using a signal filter. In an embodiment, the signal filter is based on a wavelet transform that operates simultaneously in the frequency and time domain. In an embodiment, such a wavelet filter is capable of filtering certain frequency components of the signal that belong to noise and appear at a given time, while preserving similar frequency components of the useful signal that appear at a different time. In an embodiment, the frequency spectrum of a wavelet filter replicates the frequency band of a typical N-shaped optoacoustic signal while simultaneously providing smooth window edges which do not cause signal distortions upon convolution.

In an embodiment, such a wavelet filter is useful in optoacoustic imaging in its capability to restore the original pressure profile generated in tissue prior to pressure propagation. In the course of propagation through tissue, the originally positive pressure signal converts into a bipolar (compression/tension) profile. Therefore, reconstruction of an image of absorbed optical energy (optoacoustic image) requires a transformation that starts with bipolar signals and provides for all-positive values of the optoacoustic image intensities. In an embodiment, a multi-scale wavelet filter, for example, a filter that simultaneously integrates the signal over time and provides summation of a number of frequency bands present in the signal, can convert bipolar pressure signals into monopolar signal representing thermal energy or originally generated positive pressure.

Figure 12C:
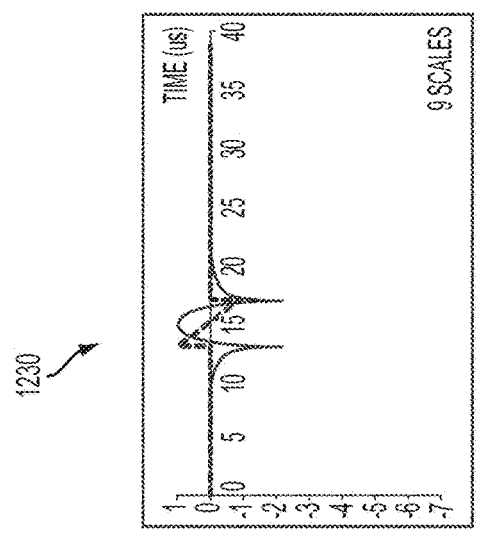
FIGS. 12A-12C provide an illustrative example of wavelet filtered N-shaped optoacoustic signals restored to their original rectangular pressure profile by summation of all scales corresponding to frequency ranges from low to high for five scales, seven scales and nine scales.
Figure 12B:
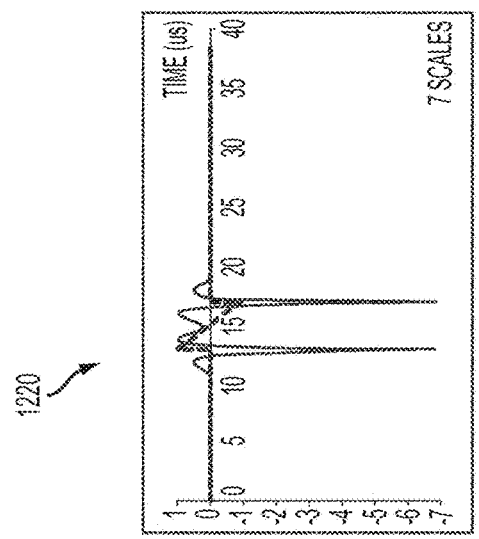
Figure 12A:
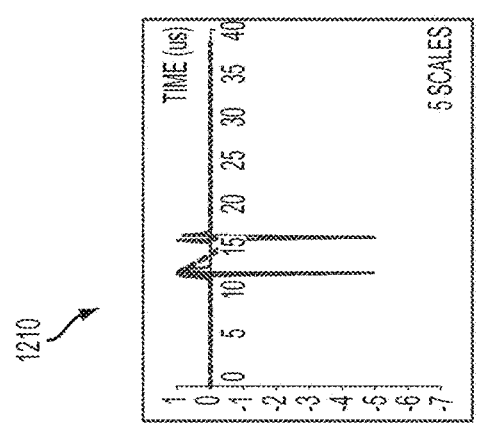

FIGS. 12A-12C provide an illustrative example of wavelet filtered N-shaped optoacoustic signals restored to their original rectangular pressure profile by summation of all scales corresponding to frequency ranges from low to high for five scales 1210, seven scales 1220 and nine scales 1230.

In various embodiments, wavelet filtering permits enhancements of objects on the image within certain range of dimensions. An imaging operator (ultrasonic technician or diagnostic radiologist) typically desires to better visualize a tumor with specific dimensions and other objects, such as blood vessels, with their specific dimensions. In an embodiment, the wavelet filter allows the operator to apply specific selection of scales of the wavelet filter than would enhance only objects of certain sizes and suppress object of other unimportant sizes. In an embodiment, boundaries can be well visualized for objects of any size, so the high-frequency wavelet scales are beneficial for the image quality and are included in the selection of scales. In an embodiment, for a mathematically correct tomographic reconstruction, a ramp filter can be applied to the signal, which can linearly enhance contribution of higher frequencies.

Image Reconstruction

In various embodiments, image reconstruction typically uses radial back-projection of processed and filtered signals onto the image plane. However, due to the limited field of view available from small hand-held probes, only an incomplete data set can be obtained. As a result, the 2D optoacoustic images may include artifacts distorting the shape and brightness of the objects displayed on the images. In an embodiment, aperture integrated normalized radial back projection is used to correct some of the reconstruction artifacts that are observed in limited aperture optoacoustic tomography.

Figure 13:
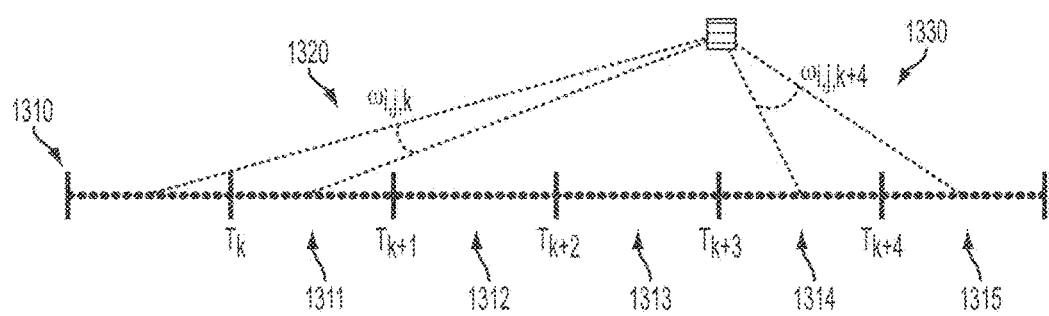
FIG. 13 provides an illustrative diagram of radial backprojection where each transducer element aperture is weighted and normalized for the total aperture of the transducer array.

FIG. 13 provides an illustrative diagram of radial back-projection where each transducer element aperture is weighted and normalized for the total aperture of the transducer array.

In an embodiment, $T_k$-$T_{k+4}$, 1311-1315, are the transducers 1310 in the array, $B_{i,j}$ is the brightness (intensity) of a pixel with coordinates (i,j), $\omega_{i,j,k}$ 1320, 1330 is the angular portion of optoacoustic wave front emitted by the pixel (i,j) as it is visualized by the transducer #k, $\Omega_{i,j}=\Sigma\omega_{i,j,k}$ (sum of all $\omega_{i,j,k}$) is the portion of the optoacoustic wave front emitted by pixel (i,j) as it is visualized by the entire transducer array, and is the sample of the optoacoustic signal measured by $k^{th}$ transducer and used in reconstruction of the brightness in the pixel (i,j). Various backpropagation algorithms can be used to normalize an optoacoustic image.

In an embodiment, a backpropagation algorithm can be expressed as:

$$B_{i,j}=\Sigma_k S_{i,j,k} \quad (1)$$

However, in at least some embodiments, aperture normalized backprojection produces superior image results. In an embodiment, the aperture normalized backprojection can be expressed as:

$$B_{i,j} = \frac{1}{\Omega i,j}\sum_k S_{i,j,k}\Omega_{i,j,k} \quad (2)$$

Figure 14A:
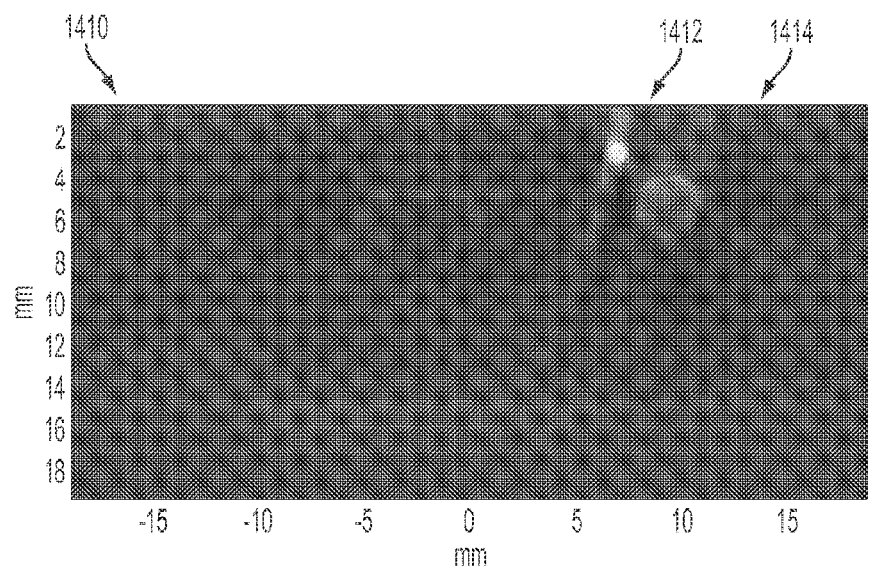
FIGS. 14A and 14B provide an illustrative example of optoacoustic tomographic images of an imaging slice through tissue with a small artery, larger vein and a rectangular grid allowing estimation of system performance in visualization of microvessels.
Figure 14B:
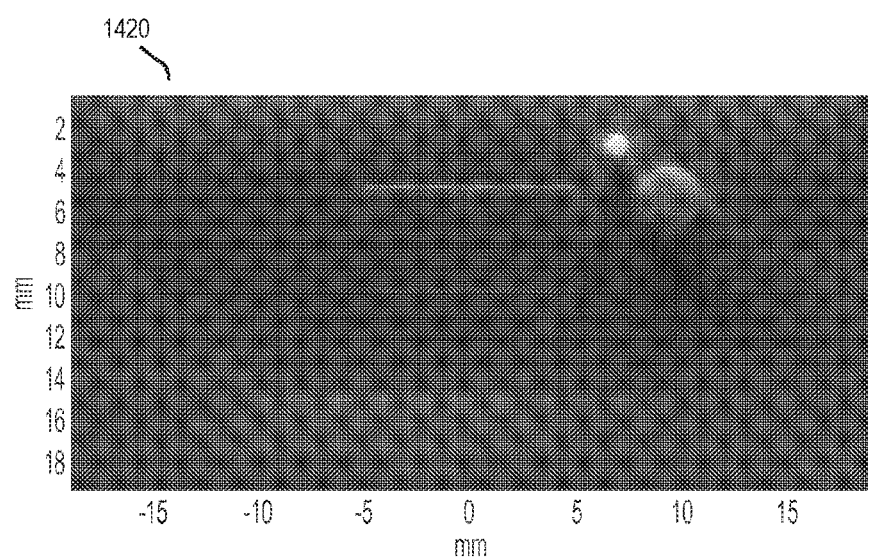

FIGS. 14A and 14B provide an illustrative example of optoacoustic tomographic images 1410 and 1420 of an imaging slice through a tumor angiogenesis model. In the first image 1410, a backpropagation algorithm, such as the first algorithm immediately above, is used to normalize the image. The resulting image has strong, bright arc-shaped artifacts 1412 around the blood vessels 1414 that are close to array surface. In the second image 1420, aperture normalized backprojection algorithm, such as the second algorithm immediately above, is used to normalize the image. As can be seen, the aperture normalized backprojection algorithm corrects image brightness and reduces the arc-shaped artifacts.

Figure 15A:
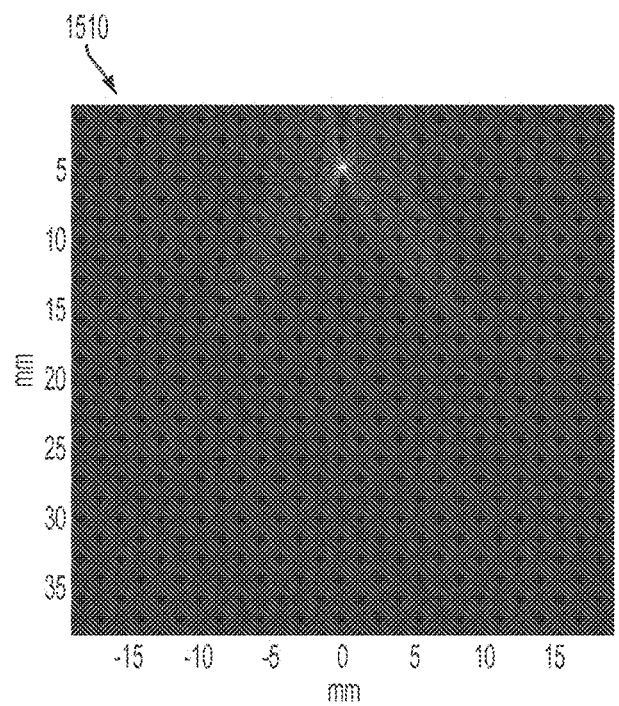
FIGS. 15A and 15B provide an illustrative example of optoacoustic tomographic images of a point spread function as visualized with a flat linear probe using a backpropagation algorithm and an aperture normalized backprojection algorithm.
Figure 15B:
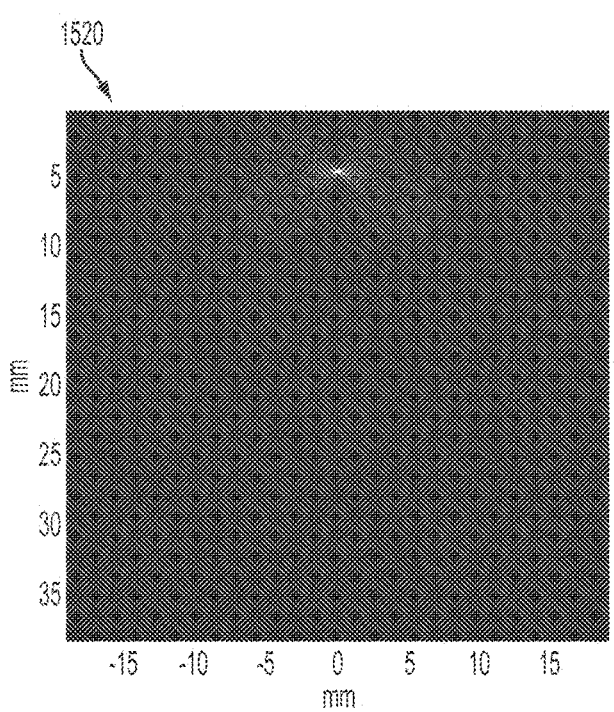

FIGS. 15A and 15B provide an illustrative example of optoacoustic tomographic images 1510 and 1520 of a point spread function as visualized with flat linear probe using 1510 a backpropagation algorithm, such as the first algorithm immediately above, and 1520 an aperture normalized backprojection algorithm, such as the second algorithm immediately above. As can be seen, the aperture normalized backprojection algorithm corrects image brightness and reduces artifacts.

Image Processing and Display

In an embodiment, the optoacoustic image palette is equalized to diminish effects of light distribution within tissue. Such equalization transforms the dynamic range of optoacoustic images for better visualization of both shallow and deep objects.

Figure 16A:
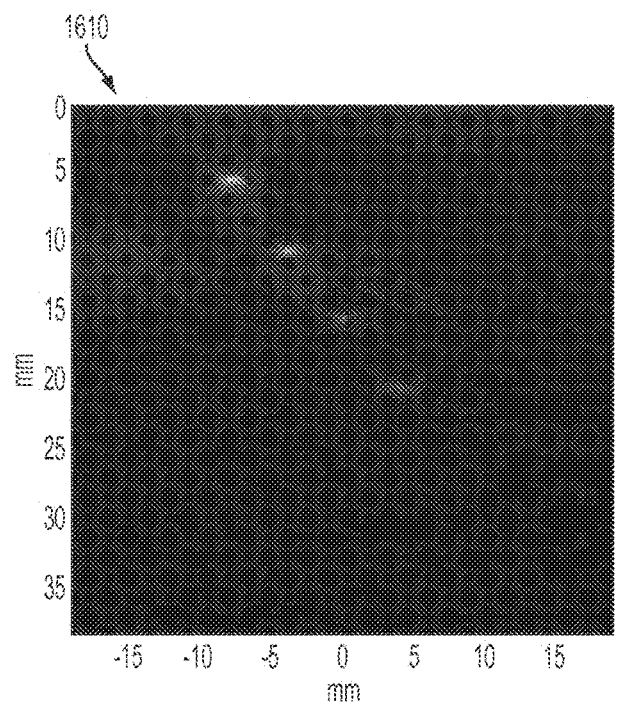
FIGS. 16A and 16B provide an illustrative example of optoacoustic images of a phantom with hairs embedded at different depths where the first image was created using an embodiment of a standard palette and the second image was created using an embodiment of a depth-normalized palette.
Figure 16B:
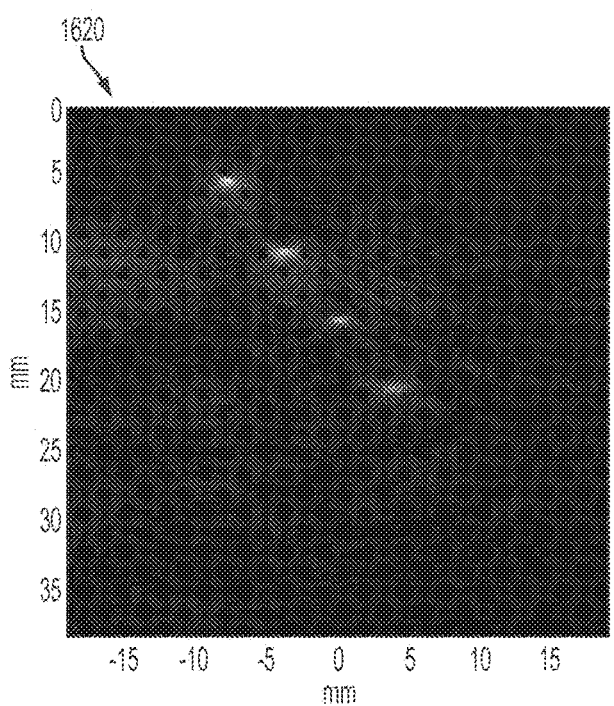

FIGS. 16A and 16B provide an illustrative example of optoacoustic images 1610 and 1620 of a phantom with hairs embedded at different depths where the first image 1610 was created using a an embodiment of a standard palette and the second image 1620 was created using an embodiment of a depth-normalized palette. As can be seen, utilizing the depth-normalized palette enhances visibility of deep objects in the illustrated embodiment.

In an embodiment, principal component analysis (PCA) on a single optoacoustic image acquisition (different channels) is used to remove cross-correlated signal noise. Principal component analysis on a dataset of optoacoustic signals can remove correlated image clutter. Principal component analysis on optoacoustic frames can also remove correlated image clutter.

Figure 17A:
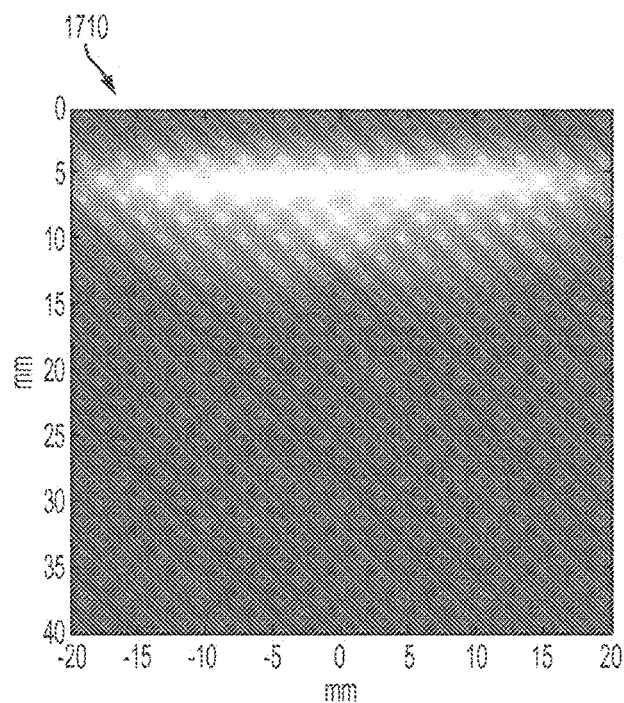
FIGS. 17A and 17B provide an illustrative example of optoacoustic images of a phantom of a spherical simulated tumor obtained with a flat linear probe.
Figure 17B:
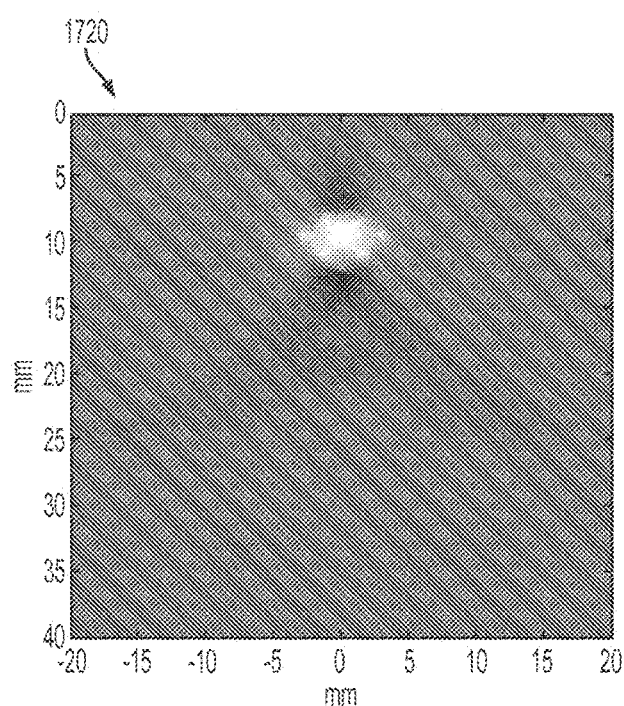

FIGS. 17A and 17B provide an illustrative example of optoacoustic images 1710 and 1720 of a phantom of a spherical simulated tumor obtained with flat linear probe. The first image 1710 is a raw image that was not subjected to principal component analysis processing. The second image 1720 has been subjected to principal component analysis processing with first principal component deconvolution. As can be seen, utilizing principal component analysis processing enhances image quality by, inter alia, reducing artifacts.

In an embodiment, design features of signal and image processing of the present disclosure can be summarized in the Table 2 as follows:

TABLE 2

Summary of signal and image processing.

| System Feature | Advantages |
| --- | --- |
| Operator-assisted boundary tracking on ultrasonic and optoacoustic images | Can improve quantitative optoacoustic diagnostics by evaluating the diagnostic parameters within the tumor boundary defined on US images<br>Diagnostics can be enhanced by morphological analysis of the tumor boundary |
| Aperture integrated normalized radial back projection | Corrects some of the reconstruction artifacts that are observed in a limited aperture optoacoustic tomography |
| Equalization of the optoacoustic image palette to diminish effects of light distribution within the tissue | Transforms dynamic range of optoacoustic images for better visualization of both shallow and deep objects |
| Principal component analysis (PCA) of the optoacoustic signal data | PCA on a single optoacoustic acquisition (different channels) is a fast and efficient way to remove cross-correlated signal noise<br>PCA on a dataset of optoacoustic signals removes correlated image clutter<br>PCA on optoacoustic frames removes correlated image clutter |
| Optoacoustic imaging system with quantitative assessment of total hemoglobin, blood oxygenation, and water | Cancer diagnostics based on those parameters or a single malignancy index (tHb*water/oxygenation) with respect to average background |
| Wavelet transform that enhances images of objects within certain dimension range | Operator can easily select the maximum size of the objects to be enhanced on the image. Everything larger will be filtered out |
| Adaptive beam-forming for optoacoustic imaging | Allows individual reconstruction on a family of radial wavelet sub-bands |

Diagnostic Image Reprocessing

Figure 18:
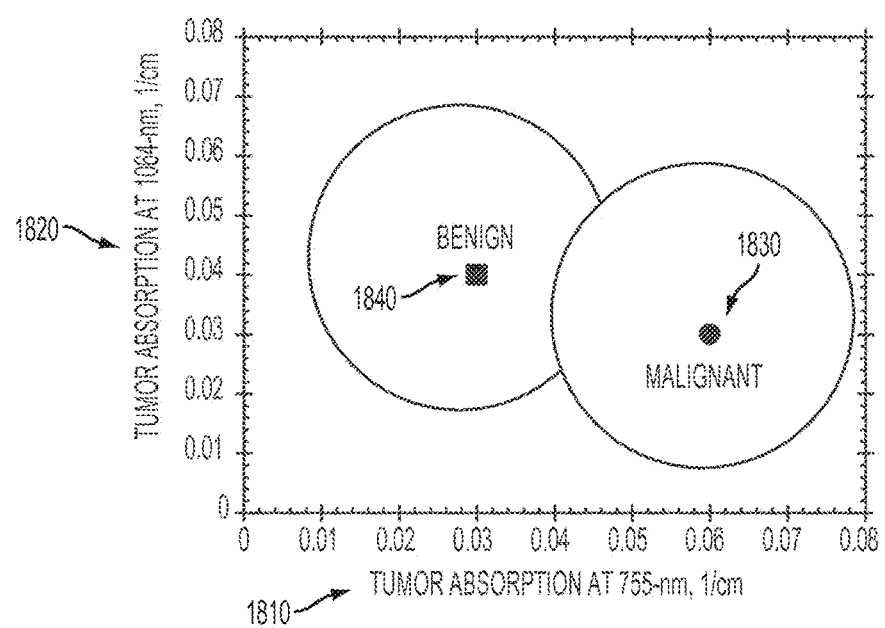
FIG. 18 shows a diagram illustrating tumor differentiation based on absorption coefficients at two wavelengths, 757 nm and 1064 nm, which match the local maximum of hemoglobin absorption like in totally in hypoxic blood (757 nm) and minimum of the ratio of absorption by hypoxic hemoglobin to absorption by oxyhemoglobin like in normally oxygenated blood (1064 nm).

The principles of functional diagnostic imaging can be based on the tumor pathophysiology. For example, malignant tumors have enhanced concentration of the total hemoglobin and reduced level of oxygen saturation in the hemoglobin of blood. In an embodiment, optoacoustic images can be reprocessed and converted into, inter alia, images of (i) the total hemoglobin [tHb] and (ii) the oxygen saturation of hemoglobin [SO2]. FIG. 18 demonstrates an example of two breast tumors FIG. 18 shows a diagram illustrating tumor differentiation based on absorption coefficients at two wavelengths, 755 nm, 1810, and 1064 nm, 1820, which match the local maximum (757 nm) and minimum (1064 nm) of the ratio of absorption by hemoglobin (hypoxic blood) to absorption by oxyhemoglobin. As can be seen, a malignant tumor, 1830, has a higher absorption coefficient at 757 nm than a benign tumor, 1840, whereas the benign tumor, 1840, has a higher absorption coefficient at 1064 nm than a malignant tumor, 1830.

Figure 19:
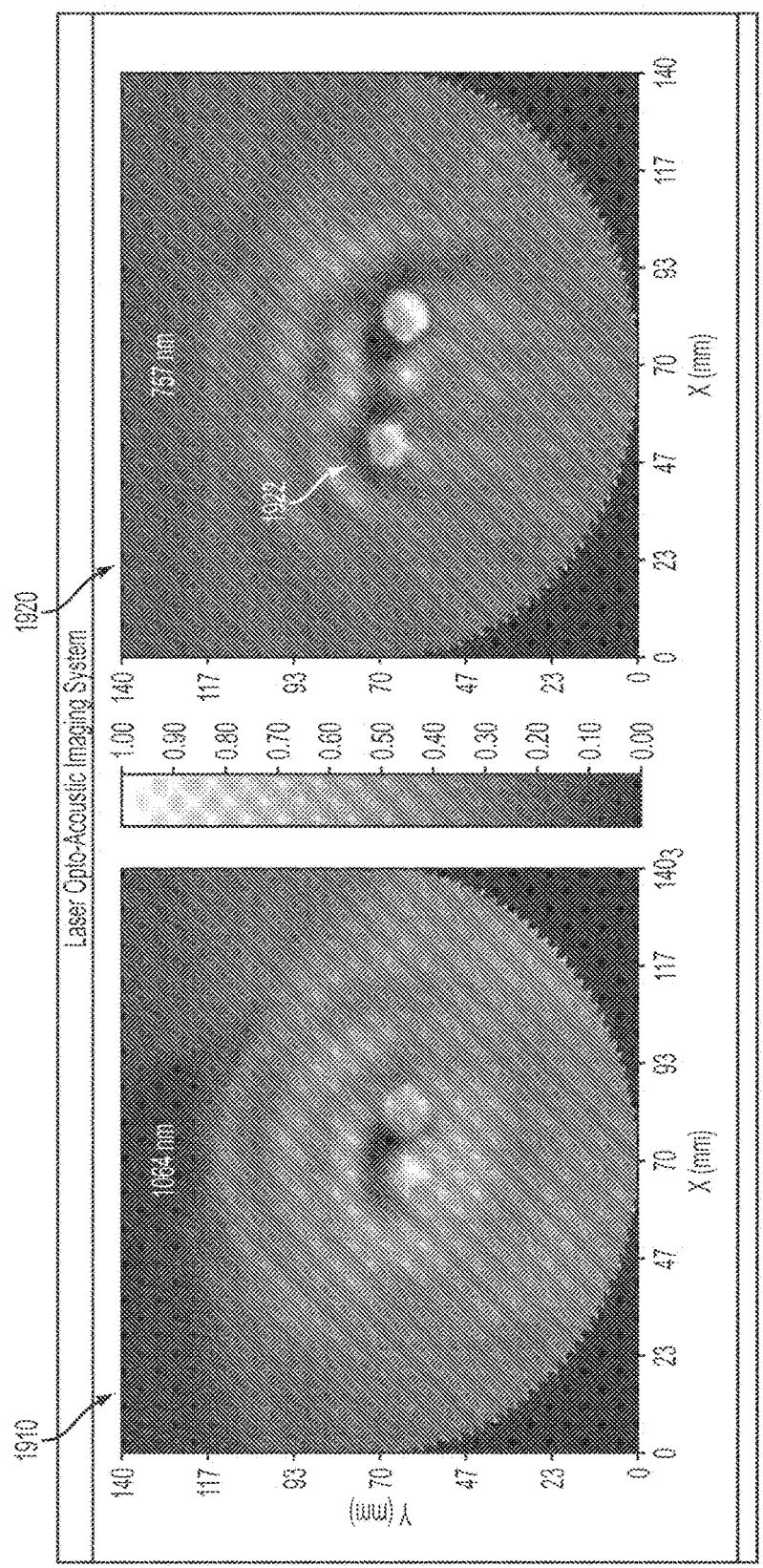
FIG. 19 illustrates tumor differentiation based on absorption coefficients at two wavelengths in a phantom simulating benign (box) and malignant (sphere) tumors.

FIG. 19 illustrates tumor differentiation by optoacoustic imaging based on absorption coefficients at two wavelengths 1910 and 1920 in a phantom. At 757 nm, 1920, a model of a malignant tumor is clearly visible, 1922, whereas the model of the malignant tumor, 1922, is not visible at 1064 nm, 1910.

Figure 20A:
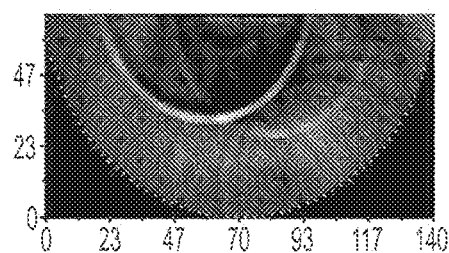
FIG. 20A shows an optoacoustic image of two intersecting tubes filled with blood having different levels of blood [SO2].
Figure 20B:
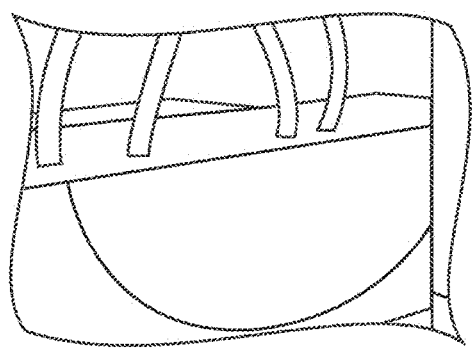
FIG. 20B shows a diagram of an experimental setup that includes artificial blood vessels placed in milk solution and imaged using arc-shaped optoacoustic probe.
Figure 20C:
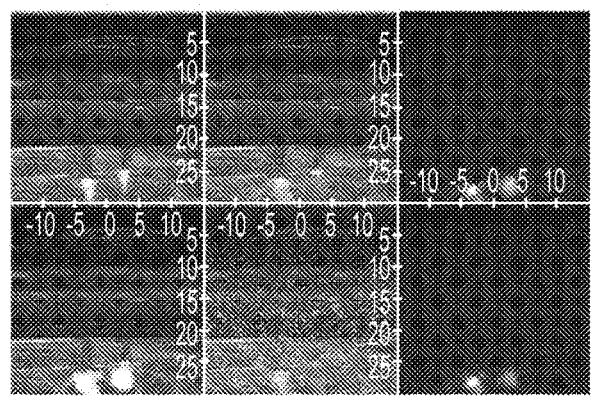
FIG. 20C shows coregistered 2D cross-sectional anatomical and functional images of blood vessel tubes showing six image panels with different anatomical and functional images.

FIG. 20A shows an optoacoustic image of two intersecting tubes filled with blood having different levels of blood [SO2] (98% in the left tube, and 31% in the right tube). The tubes were placed in 1% fat milk with optical properties similar to those found in the human breast. The wavelength of laser illumination used for this image is 1064 nm. FIG. 20B shows a diagram of an experimental setup that includes artificial blood vessels placed in milk solution and imaged using arc-shaped optoacoustic probe. FIG. 20C shows coregistered 2D cross-sectional anatomical and functional images of blood vessel tubes showing six image panels: (1—upper left) ultrasound image depicting anatomy of the body with vessels; (2—upper right) optoacoustic image obtained at the wavelength of 757 nm; (3—lower right) optoacoustic image obtained at the wavelength of 1064 nm; (4—lower left) functional image of the total hemoglobin [tHb]; (5—lower center) functional image of the blood oxygen saturation [SO2]; (6—upper center) functional image of the blood oxygen saturation presented only in the area of maximum concentration of the total hemoglobin. Raw optoacoustic images depicted in FIG. 20C in the upper right and lower right panels demonstrate different brightness of blood vessels having blood with different level of the total hemoglobin concentration [tHb] and blood oxygen saturation [SO2], accurate quantitative measurements could be performed under conditions of normalized fluence of the optical illumination of tissue in the body as a function of depth. These optoacoustic images were used to reconstruct functional images of the total hemoglobin [tHb] and the blood oxygenation [SO2]. All functional images displayed in FIG. 20C are coregistered and superimposed with the anatomical image of tissue structure for better correlation of features.

Figure 21A:
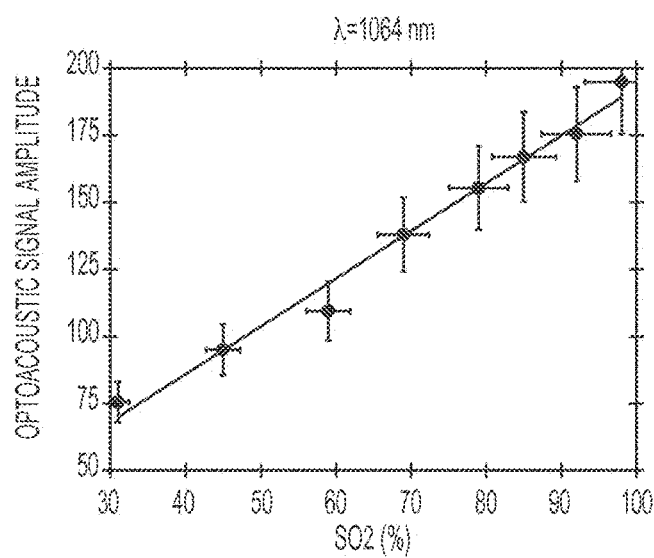
FIGS. 21A and 21B show optoacoustic signal amplitude as a function of blood oxygen saturation (with constant hematocrit) under laser illumination at a wavelength of 1064 nm in FIG. 21A and at 757 nm in FIG. 21B. These plots illustrate that blood oxygen saturation can be monitored with optoacoustic imaging.
Figure 21B:
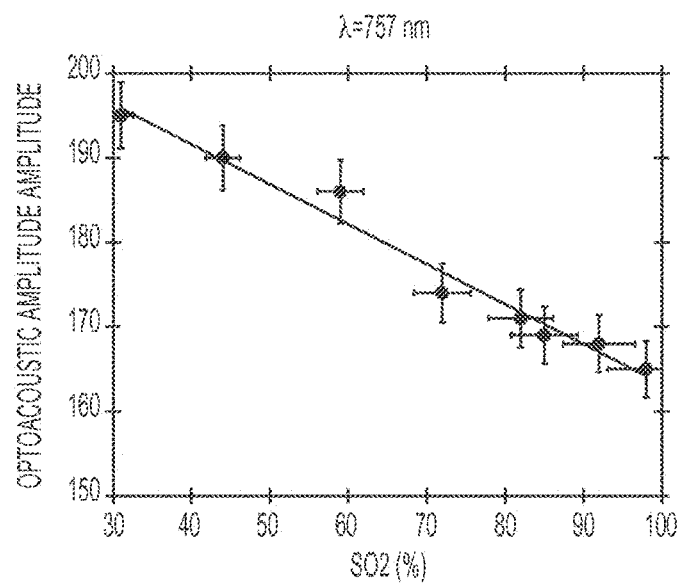

FIGS. 21A and 21B show optoacoustic signal amplitude as a function of blood oxygen saturation (with constant hematocrit) under laser illumination at the wavelength of 1064 nm in FIG. 21A and at 757 nm in FIG. 21B. These plots illustrate that blood oxygen saturation can be monitored with optoacoustic imaging. Specifically, this embodiment illustrates quantitative data based on measurements of the optoacoustic signal amplitude in blood having various levels of oxygen saturation (from 30% to 98%) and hematocrit of 38 g/dL of hemoglobin [tHb] in erythrocytes. As predicted by the published absorption spectra of blood, the optoacoustic signal amplitude at 1064 nm illumination increases with increased level of oxygen saturation, while the optoacoustic signal amplitude decreases with increased blood oxygenation at 757 nm illumination wavelength.

Figure 22:
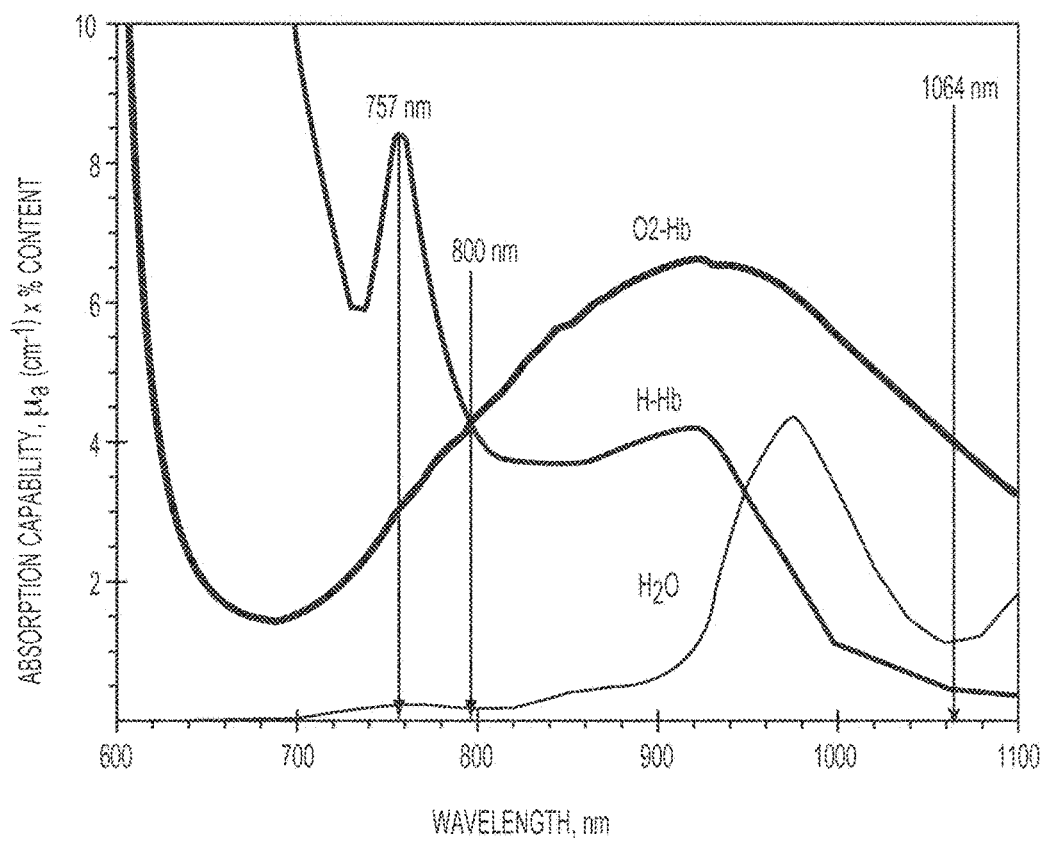
FIG. 22 illustrates optical absorption spectra of the main tissue chromophores absorbing optical energy in the near-infrared range: hemoglobin, oxyhemoglobin and water.

FIG. 22 illustrates optical absorption spectra of the main tissue chromophores absorbing optical energy in the near-infrared range: hemoglobin, oxyhemoglobin and water. Preferred laser wavelengths for functional imaging are 757 nm and 1064 nm matching max and min ratio of [HHb]/[O2Hb], while the wavelength of 800 nm is the best for calibration purposes through measurements of the total hemoglobin [tHb].

Figure 23A:
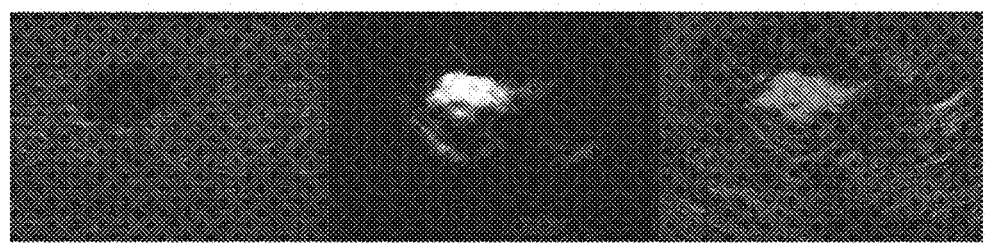
FIGS. 23A and 23B illustrate coregistered functional and anatomical imaging of breast tumors in phantoms accurately replicating optical and acoustic properties of an average breast with tumors.
Figure 23B:
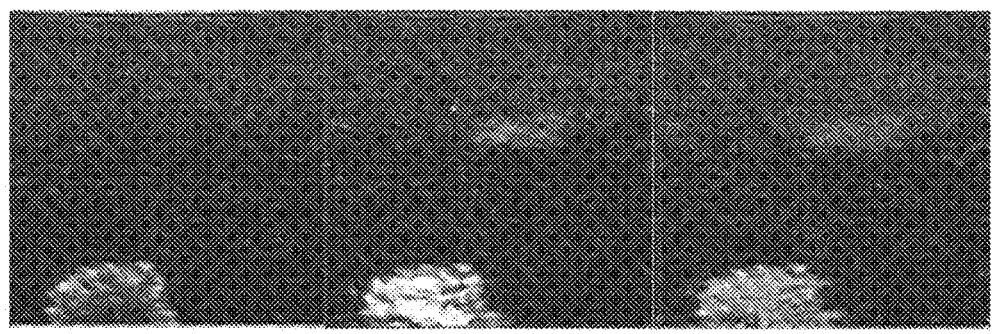

FIGS. 23A and 23B illustrate coregistered functional and anatomical imaging of breast tumors in phantoms accurately replicating optical and acoustic properties of an average breast with tumors. FIG. 23A shows 2D images of: model of malignant tumor morphology based on ultrasound (left), the same anatomical image coregistered with functional image of the total hemoglobin concentration (center) and with functional image of the blood oxygenation (right). FIG. 23B shows 2D images of a model benign tumor: morphology image based on ultrasound (left), the same anatomical image coregistered with functional image of the total hemoglobin concentration (center) and with functional image of the blood oxygenation (right).

Figure 24A:
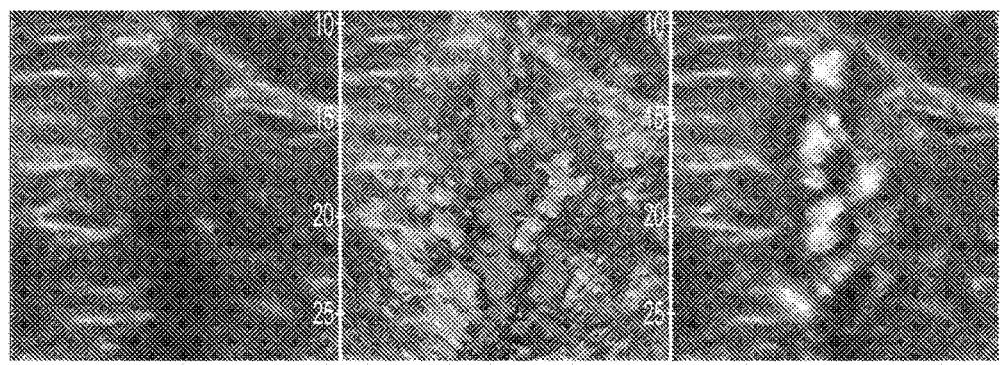
FIGS. 24A and 24B illustrate coregistered functional and anatomical imaging of breast tumors.
Figure 24B:
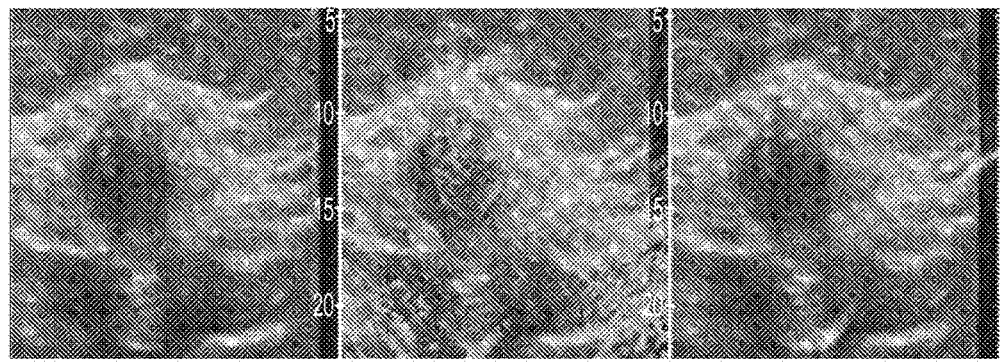

FIGS. 24A and 24B illustrate coregistered functional and anatomical imaging of breast tumors. FIG. 24A shows 2D images of invasive ductal carcinoma, a malignant tumor with rough boundaries, heterogeneous morphology, high concentration of total hemoglobin and low oxygen saturation (hypoxia). The malignant tumor morphology is based on ultrasound in the left image, and the same anatomical image coregistered with functional image of the blood oxygenation in the center image and with functional image of the total hemoglobin concentration in the right image. FIG. 24B shows 2D images of a breast with Fibroadenoma, a benign tumor with relatively round boundaries, normal concentration of oxyhemoglobin and relatively low total hemoglobin. Breast morphology is based on ultrasound in the left image, and the same anatomical image is coregistered with a functional image of the blood oxygenation in the center image and with a functional image of the total hemoglobin concentration in the right image.

CONCLUSION

While some embodiments can be implemented in fully functioning computers and computer systems, various embodiments are capable of being distributed as a computing product in a variety of forms and are capable of being applied regardless of the particular type of machine or computer-readable media used to actually effect the distribution.

At least some aspects disclosed can be embodied, at least in part, in software. That is, the techniques described herein may be carried out in a special purpose or general purpose computer system or other data processing system in response to its processor, such as a microprocessor, executing sequences of instructions contained in a memory, such as ROM, volatile RAM, non-volatile memory, cache or a remote storage device.

Routines executed to implement the embodiments may be implemented as part of an operating system, firmware, ROM, middleware, service delivery platform, SDK (Software Development Kit) component, web services, or other specific application, component, program, object, module or sequence of instructions referred to as "computer programs." Invocation interfaces to these routines can be exposed to a software development community as an API (Application Programming Interface). The computer programs typically comprise one or more instructions set at various times in various memory and storage devices in a computer, and that, when read and executed by one or more processors in a computer, cause the computer to perform operations necessary to execute elements involving the various aspects.

A machine-readable medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. Further, the data and instructions can be obtained from centralized servers or peer-to-peer networks. Different portions of the data and instructions can be obtained from different centralized servers and/or peer-to-peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not required that the data and instructions be on a machine-readable medium in entirety at a particular instance of time.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROMS), Digital Versatile Disks (DVDs), etc.), among others.

In general, a machine readable medium includes any mechanism that provides (e.g., stores) information in a form accessible by a machine (e.g., a computer, network device, personal digital assistant, manufacturing tool, any device with a set of one or more processors, etc.).

In various embodiments, hardwired circuitry may be used in combination with software instructions to implement the techniques. Thus, the techniques are neither limited to any specific combination of hardware circuitry and software nor to any particular source for the instructions executed by the data processing system.

Although some of the drawings illustrate a number of operations in a particular order, operations that are not order dependent may be reordered and other operations may be combined or broken out. While some reordering or other groupings are specifically mentioned, others will be apparent to those of ordinary skill in the art and so do not present an exhaustive list of alternatives. Moreover, it should be recognized that the stages could be implemented in hardware, firmware, software or any combination thereof.

In the foregoing specification, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

The invention claimed is:

1. An imaging system for visualization of slices into a depth of tissue of at least a portion of a body, comprising:
   a hand-held imaging probe comprising an array of ultrasonic transducers and a light emitting portion, wherein the light emitting portion comprises:
      a first fiber-optic bundle and a first light diffuser configured to form a first light beam and a second fiber-optic bundle and a second light diffuser configured to form a second light beam, wherein the first and second fiber-optic bundles are disposed on opposite sides of the array of ultrasonic transducers; and
   a processing system configured to receive data originating from the hand-held imaging probe and to process at least three independent images based at least in part upon said data, wherein the processing comprises deconvolution of an impulse response associated with the array of ultrasonic transducers, the impulse response based on a delta-function ultrasonic signal generated by laser pulses in an absorbing optical medium the three independent images together comprising:
      a first functional image reflecting distribution of total hemoglobin concentration;
      a second functional image reflecting distribution of blood oxygen saturation; and
      a morphological image of tissue structures.

2. The imaging system of claim 1, further comprising a signal filter that filters the delta-function ultrasonic signal after deconvolution of the impulse response associated with the array of ultrasonic transducers and communicates with the processing system.

3. The imaging system of claim 2, wherein the signal filter is a wavelet filter based on a wavelet transform that operates simultaneously in the frequency and time domain.

4. The imaging system of claim 3, wherein the wavelet filter is configured to filter frequency components of the delta-function ultrasonic signal that are noise at a first time; and preserve frequency components of the delta-function ultrasonic signal at a second time.

5. The imaging system of claim 3, wherein a frequency spectrum of the wavelet filter replicates a frequency band of an N-shaped optoacoustic signal.

6. The imaging system of claim 5, wherein the wavelet filter provides smooth window edges that do not cause signal distortions upon convolution.

7. The imaging system of claim 5, wherein the wavelet filter converts bipolar pressure signals into monopolar signals.

8. The imaging system of claim 1, wherein the deconvolution of the impulse response restores N-shaped pressure signals.

9. The imagining system of claim 1, wherein the hand-held imaging probe has a concave arc shape.

* * * * *